US012784896B2

(12) United States Patent
Chen et al.

(10) Patent No.: US 12,784,896 B2
(45) Date of Patent: Nov. 3, 2026

(54) ADVANCING VOLUMETRIC MEDICAL IMAGE SEGMENTATION VIA GLOBAL-LOCAL MASKED AUTOENCODER

(71) Applicant: The Hong Kong University of Science and Technology, Hong Kong (CN)

(72) Inventors: Hao Chen, Hong Kong (CN); Jiaxin Zhuang, Hong Kong (CN); Luyang Luo, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 189 days.

(21) Appl. No.: 18/741,505

(22) Filed: Jun. 12, 2024

(65) Prior Publication Data

US 2025/0022580 A1 Jan. 16, 2025

Related U.S. Application Data

(60) Provisional application No. 63/512,905, filed on Jul. 10, 2023.

(51) Int. Cl.
*G16H 30/40* (2018.01)
*G06T 3/40* (2024.01)
(Continued)

(52) U.S. Cl.
CPC ............... *G16H 30/40* (2018.01); *G06T 3/40* (2013.01); *G06T 7/10* (2017.01); *G06T 9/00* (2013.01);
(Continued)

(58) Field of Classification Search
CPC .. G16H 30/40; G06T 3/40; G06T 7/10; G06T 9/00; G06T 15/00; G06T 2207/20081;
(Continued)

(56) References Cited

U.S. PATENT DOCUMENTS

2014/0253555 A1* 9/2014 Lum ..................... G06T 15/005 345/428
2021/0133581 A1* 5/2021 Podgorny ............ G10L 15/183
(Continued)

FOREIGN PATENT DOCUMENTS

CN 114822548 A 7/2022
CN 115690115 A 2/2023
(Continued)

OTHER PUBLICATIONS

Chen, Zekai, et al. "Masked Image Modeling Advances 3d Medical Image Analysis," *Proceedings of the IEEE/CVF Winter Conference on Applications of Computer Vision*, pp. 1970-1980, (2023).
(Continued)

*Primary Examiner* — Qun Shen
(74) *Attorney, Agent, or Firm* — LEYDIG VOIT & MAYER, LTD

(57) ABSTRACT

A system is provided for training a neural network model. The system comprises one or more image acquisition devices, configured to obtain volumetric image data; and one or more processors, configured to: generate images of a plurality of views, which comprise a global complete view and one or more masked views; generate, by a Global-Local Masked AutoEncoder (GL-MAE) encoder system, representations corresponding to the global complete view and the one or more masked views; generating one or more reconstructed images corresponding to the one or more masked views; evaluating in a shared representation space, consistency between the representations of the global complete view and the one or more masked views; computing one or more losses based on the one or more reconstructed images and the results from the consistency evaluation; and updating one or more parameters in the neural network model based on the one or more losses.

20 Claims, 8 Drawing Sheets

(51) Int. Cl.
*G06T 7/10* (2017.01)
*G06T 9/00* (2006.01)
*G06T 15/00* (2011.01)
*G06V 10/25* (2022.01)

(52) U.S. Cl.
CPC .............. *G06T 15/00* (2013.01); *G06V 10/25* (2022.01); *G06T 2207/20081* (2013.01); *G06T 2207/20084* (2013.01)

(58) Field of Classification Search
CPC ....... G06T 2207/20084; G06T 2210/41; G06T 2207/20132; G06T 7/11; G06T 15/20; G06V 10/25; G06V 10/82; G06N 3/00; G06N 3/045
See application file for complete search history.

(56) References Cited

U.S. PATENT DOCUMENTS

| | | | | |
|---|---|---|---|---|
| 2021/0382497 | A1* | 12/2021 | Zhi | G06T 7/174 |
| 2022/0138932 | A1 | 5/2022 | Bonakdar Sakhi et al. | |
| 2022/0276625 | A1* | 9/2022 | Metzger | G05B 15/02 |
| 2023/0376729 | A1* | 11/2023 | Zhou | G06N 3/0895 |
| 2023/0410483 | A1* | 12/2023 | Chen | G06V 10/7753 |
| 2024/0010227 | A1* | 1/2024 | Gyllenhammar | G06V 10/7792 |
| 2024/0311987 | A1* | 9/2024 | Schwartz | G06N 3/0455 |

FOREIGN PATENT DOCUMENTS

| | | | | |
|---|---|---|---|---|
| CN | 115861306 A | 3/2023 | | |
| CN | 11668673 A | 9/2023 | | |
| CN | 117095267 A | 11/2023 | | |
| WO | WO-2021222601 A1 * | 11/2021 | | G16H 50/80 |
| WO | WO 2023/211525 A1 | 11/2023 | | |

OTHER PUBLICATIONS

Zhou, Zongwei, et al. "Models Genesis" *Medical Image Analysis*, pp. 1-26, (2020).

Tang, Yucheng, et al. "Self-Supervised Pre-Training of Swin Transformers for 3D Medical Image Analysis." *Proceedings of the IEEE/CVF Conference on Computer Vision and Pattern Recognition*, pp. 1-16, (2022).

Chen, Ting, et al. "A Simple Framework for Contrastive Learning of Visual Representations," *Proceedings of the 37th International Conference on Machine Learning*, 11 pages total, (2020).

Caron, Mathilde, et al., "Unsupervised Learning of Visual Features by Contrasting Cluster Assignments". *Advances in Neural Information Processing Systems*, 33:9912-9924, (13 pages total) 2020.

Chatitanya, Krishna, et al., "Constrastive learning of global and local features for medical image segmentation with limited annotations", *Advances in Neural Information Processing Systems*, 33:12546-12558, 2020.

Chen, Xinlei et al., "*Exploring Simple Siameses Representation Learning*", in *arXiv preprint ar Xiv*:2011.10566v1, 2020.

Fan, Hehe, et at., "Self-Supervised Global-Local Structure Modeling for Point Cloud Domain Adaption with Reliable Vote Pseudo Labels", *In Proceedings of the IEEE/CVF Conference on Computer Vision and Pattern Recognition*, pp. 6377-6386, 2022.

Gao, Yuting, et al., "DisCo: Remedying Self-Supervised Learning on Lightweight Models with Distilled Contrastive Learning", *In ECCV*, pp. 237-253, Springer 2022.

Gao, Peng, et al., "MCMAE: Masked-Convolution Meets Masked Autonencoders" *36th Conference on Neural Information Processing Systems* (*NurIPS 2022*), 13 pages total.

Henaff, Olivier, "Data-Efficient Image Recognition with Contrastive Predictive Coding", *In ICML*, pp. 4182-4192, 2020.

Komodakis, Nikos, et al., "Unsupervised Representation Learning by Predicating Image Rotations", *In ICLR*, 2018.

Chen, Ting et al., "Big Self-Supervised Models are Strong Semi-Supervised Learners", *In NeurIPS*, pp. 22243-22255, 2020.

Chen, Xinlei, et al., "Improved Baseline with Momentum Contrastive Learning", *In CVPR*, pp. 9729-9738, 2020.

Liu, Ze, et al., "Swin Transformer: Hierarchical Vision Transformer using Shifted Windows", *In Proceedings of the IEEE/CVF international conference on computer vision*, pp. 10012-10022, 2021.

Pathak, Deepak, et al., "Context encoders: Feature learning by in painting", *In Proceedings of the IEEE Conference on Computer Vision and Pattern Recognition*, pp. 2536-2544, 2016.

Simpson, Amber L., et al., "A large annotated medical image dataset for the development and evaluation of segmentation algorithms", *arXiv preprint arXiv:190.09063*, pp. 1-15, (2019).

Taleb, Aiham, et al., "3D Self-Supervised Methods for Medical Imaging", *NeurIPS*, 33:18158-18172, 2020.

Vincent, Pascal, et al. "Stacked Denoising Autoencoders: Learning Useful Representations in a Deep Network with Local Denoising Criterion", *Journal of machine Learning Research*, 11(12), pp. 3371-3408, (2010).

Tao, Xing et al. "Revisiting Rubik's Cube Self-supervised Learning with Volume-wise Transformation for 3D Medical Image Segmentation", *In Medical Image computing an computer Assisted intervention—MICCAI 2020: 23rd International Conference*, Lima, Peru, Oct. 4-8, 2020, Proceedings, Part IV 23, pp. 238-248, Springer 2020, (arXiv:2007.08826).

Wang, Jinpeng, et al., "Enhancing Unsupervised Video Representation Learning by Decoupling the Scene and the Motion", *The Thirty-Fifth AAAI Conference on Artificial Intelligence* (*AAAI—21*), pp. 10129-10137, (2020).

Xie, Yutong, et al., "PGL: Prior-Guided Local Self-Supervised Learning for 3D Medical Image Segmentation", *arXiv preprint arXiv:2011.12640*, 2020.

Xie, Zhenda, et al., SimMIM: A Simple Framework for Masked Image Modeling: *In CVPR*, pp. 9653-9663, 2022.

Zheng, Hao et al., "Hierarchical Self-Supervised Learning for Medical Image Segmentation Bases on Multi-Domain Data Aggregation", In *Medical Image Computing and Computer Assisted Intervention—MICCAI 2021: Proceedings, Part I* 24, pp. 622-632, Springer, (2021), arXiv:2107.04886 [cs.CV].

Zhou, Hong-Yu, et al., "A Unified Visual Information Preservation Framework for Self-Supervised Pre-Training in Medical Image Analysis", *IEEE Transactions on Pattern Analysis and Machine Intelligence*, (2023).

Zhang, Yundong, et al., "TransFuse: Fusing Transformers and CNNs for Medical Image Segmentation", *in MICCAI*, pp. 14-24, Springer (2021).

Zhang, Tong, et al., "Leverage Your Local and Global Representations: A New Self-Supervised Learning Strategy", *In Proceedings of the IEEE/CVF Conference on Computer Vision and Pattern Recognition*, pp. 16580-16589, 2022.

Xu, Minghao, et al., "Self-Supervised Graph-Level Representation Learning with Local and Global Structure", *In International Conference on Machine Learning*, pp. 11548-11558, PMLR, 2021. (arXiv:21-6.04113v1 2021).

Sharir, Gilad, et al., "An Image is Worth 16x16 Words, What is a Video Worth?", *arXiv reprinting arXiv*:2103.13915, pp. 1-11 (2021).

Noroozi, Mehdi, et al., "Unsupervised Learning of Visual Representations by Solving Jigsaw Puzzle", *In ECCV*, pp. 69-84, 2016.

Caron, Mathilde, et al., "Deep Clustering for Unsupervised Learning of Visual Features", *In Proceedings of the European Conference on Computer Vision*, (*ECCV*), pp. 132-149 (2018).

Chen, Zekai et al., "Masked Image Modeling Advances 3D Medial Image Analysis", *In WACV*, pp. 1970-1980, 2023.

Caron, Mathilde, et al., "Emerging Properties in Self-Supervised Vision Transformers", *In ICCV*, pp. 9650-9660, (2021).

Chen, Liang et al., "Self-supervised learning for medical image analysis using image context restoration", *Medical Image Analysis*, 58:101539, 2019.

Grill, Jean-Bastien, et al., "Bootstrap Your Own Latent: A New Approach to Self-Supervised learning", *In NeurIPS*, pp. 21271-21284, 2020.

Haghighi, Fatemeh, et al., "DiRA: Discriminative, Restorative, and Adversarial Learning for Self-Supervised Medical Image Analysis",

(56) References Cited

OTHER PUBLICATIONS

*In Proceedings of the IEEE/CVF Conference on Computer Vision and Pattern Recognition*, pp. 20824-20834, (2022.).
Hatamizadeh, Ali, et al., "UNETR: Transformers for 3D Medical Image Segmentation", *In Proceedings of the IEEE/CVF Winter Conference on Applications of Computer Vision*, pp. 574-584, 2022.
He, Kaiming, et al., "Masked Autoencoder are Scalable Vision Learners", *In CVPR*, pp. 16000-16009, 2022.
Jin, Cheng, et al., "Label-Efficient Deep, Learning in Medical Image Analysis: Challenges and future directions", *arXiv preparing arXiv:2303.12484*, 2023.
Tajbakhsh, Nima, et al., "Embracing Imperfect Datasets: A Review of Deep Learning Solutions for Medical Image Segmentation", *Medical Image Analysis*, 63:101693, arXiv:1908.10454, 2020.
Shen, Dinggang, et al., "Deep learning in Medical image analysis", *Annual review of biomedical engineering*:, 19:221-248, 2017.
Chen, Mark et al., "Generative pretraining from Pixels", *In International Conference on Machine Learning*, pp. 1691-1703, PMLR, 2020.
Kingma, Diederik P., et al., "Adam: A method for stochastic optimization", *arXiv reprinting arXiv*:1412.6980, pp. 1-11, (2014).
Asano, Yuki M., et al., "Self-labelling via simultaneous clustering and presentation learning", *arXiv preprint arXiv*:1911.05371, 2019.
Hendrycks, Dan, et al., "*Gaussian Error Linear Units* (*GELUs*)", arXiv preprint arXiv:1606.08415v5, 2023.
Dosovitskiy, Alexey, et al., "An Image is Worth 16x16 Words: Transformers for Image Recognition at Scale", *ICLR*, 2020.
Wang, Jinpeng, et al., "Removing the Background by Adding the Background: Towards Background Robust Self-Supervised Video Representation Learning", 2020. *arXiv*:2009.05769.
Devlin, Jacob, et al., "BERT: Pre-training of Deep Bidirectional Transformers for Language Understanding", *arXiv preprint arXiv*:1810.04805, 2018.
He, Kaiming, et al., Momentum contrast for unsupervised visual representation learning,*In CVPR*, pp. 9729-9738, 2020.
Jing, Longlong et al., "Self-supervised Visual Feature Learning with Deep Neural Networks: A Survey", *IEEE transactions on pattern analysis and machine intelligence*, 42(11):4037-4058, 2020.
Tang, Yucheng, et al., "Self-Supervised Pre-Training of Swin Transformers for 3D Medical Image Analysis", *In CVPR*, pp. 20730-20740, 2022.
Azizi, Shekoofeh, et al. "Big Self-Supervised Models Advance Medical Image Classification", *In ICCV*, pp. 3478-3488, 2021.
Zhu, Jiuwen, et al. "Rubik's cute+: A Self-Supervised Feature Learning Framework for 3d Medical Image Analysis", *Medical Image Analysis*, 64:101746, 2020.
Zhuang, Xiahai, et al., "Multivariate Mixture Model for Myocardial Segmentation Combining Multi-Source Images", *IEEE TPAMI*, 41(12):2933-2946, (2019), arXiv:1612.08820 [cs.CV]. 19 Nov.
Roth, Holger R., et al., "*Rapid artificial intelligence solution s in a pandemic—the COVID-19-20 Lung CT Lesion Sementation Challenge*," Medical Image Analysis 82(2022) 102605, (12 pages total).
Landman, Bennett, et al., "MICCAI multi-atlas labeling beyond the cranial vault-workshop and challenge", *In MICCAI Workshop*, vol. 5, p. 23, 2015, retrieved from https://www.synapse.org/Synapse:syn3193805/wiki/217752.
Myronenko, Andriy, et al., "3d MRI brain tumor segmentation using atuoencoder regularization", *In Brainlesion: Blioma, Multiple Sclerosis, Storke and Traumatic Brain Injuries, 4th International Workshop, BrainLes* 2018, Held in Conjunction with MICCAI 2018, Granada, Spain, Sep. 16, 2018, Revised Selected Papers Part II 4, pp. 311-320, Springer, 2019, arXiv:1810.11654V3 [CS.cv1] 2018.
Shen, Dinggang, et al., "Deep learning in Medical image analysis", *Annual review of biomedical engineering*:, 19:221-248, 2017, published in final edits as *Adv Exp Med Biol.* 2020.
Zhao, Ziteng, et al., "Unsupervised Constrastive Learning of Radiomics and deep Features for Label-efficient tumor classification", *In Medical Image Computing and Computer Assisted Intervention, MICCAI 2021: 24th International Conference*, Strasbourg, France, Sep. 27-Oct. 1, 2021, Proceedings, Part I 24, pp. 252-261, Springer, (2021).
Ye, Yiwen, et al., "Desd: Self-Supervised Learning with Deep Self-Distillation for 3D Medical Image Segmentation", *In Medical Image Computing and Computer Assisted Intervention—MICCAI 2022: 25th International Conference*, Singaprore, Sep. 18-22, 2022, Proceedings, Part IV, pp. 545-555, Springer, 2022.
Peng, An, et al., "CT images in Covid-19 dataset", *The Cancer Imaging Archive*, 10, 2020, retrieved from https://www.cancerimagingarchive.net/collection/ct-images-in-covid-19/.
Van Rikxoort, Eva M., "Automatic Lung Segmentation from Thoracic Computed Tomography Scans Using a Hybrid Approach with Error Detection", *Medical physics*, 36(7):2934-2947, 2009.
Touvron, Hugo, et al., "LLaMA: Open and Efficient Foundation Language Models", *arXiv preprint arXiv*:2302.13971, 2023.

* cited by examiner

700

| Paradigm | Method | Conference | →BTCV | | | →MSD Spleen | | | →MM-WHS | | |
|---|---|---|---|---|---|---|---|---|---|---|---|
| | | | 25% | 50% | 100% | 25% | 50% | 100% | 25% | 50% | 100% |
| SL | 3D U-Net (Ronneberger, Fischer, and Brox 2015) | MICCAI 2015 | 59.45 | 73.01 | 79.53 | 80.28 | 91.68 | 93.71 | 66.19 | 79.52 | 83.09 |
| | Segresnet (Myronenko 2019) | MICCAIW 2016 | 31.05 | 71.42 | 79.97 | 78.32 | 91.85 | 94.10 | 63.62 | 80.94 | 83.25 |
| | UNETR | WACV 2022 | 58.99 | 73.17 | 79.61 | 84.57 | 92.23 | 94.20 | 66.14 | 80.10 | 83.85 |
| SSL | ModelGen (Zhou et al. 2021b) | MIA 2021 | 54.18 | 61.26 | 81.45 | 85.65 | 93.02 | 94.40 | 72.28 | 81.33 | 86.36 |
| | VicRegl (Bardes, Ponce, and LeCun 2022) | NeurIPS 2022 | - | - | - | - | - | - | - | - | 84.72 |
| | Swin-UNETR (Tang et al. 2022) | CVPR 2022 | 63.96 | 75.15 | 81.54 | 88.56 | 93.54 | 95.02 | 70.74 | 81.66 | 87.06 |
| | JSSL (Nguyen et al. 2023) | AAAI 2023 | - | - | - | - | - | - | - | - | 84.89 |
| | GLSV (He et al. 2023) | CVPR 2023 | 40.20 | 46.84 | 55.72 | 89.05 | 94.20 | 95.47 | 74.51 | **85.08** | 87.07 |
| | MAE3D (Chen et al. 2023) | WACV 2023 | 66.08 | 75.39 | 81.74 | 89.65 | 94.20 | 95.20 | 69.78 | 84.64 | 86.03 |
| | GL-MAE (Ours) | - | **66.44** | **76.37** | **82.33** | **90.65** | **94.36** | **95.72** | **76.16** | 83.72 | **88.88** |

*Fig. 7*

800

| Metric | Dice score(%)↑ | | | Normalized surface dice(%)↑ | | | Hausdorff distance-95↓ | | |
|---|---|---|---|---|---|---|---|---|---|
| Setting | Baseline | MAE3D | GL-MAE | Baseline | MAE3D | GL-MAE | Baseline | MAE3D | GL-MAE |
| Linear | - | 78.36 | 80.22 | - | 38.79 | 41.47 | - | 16.41 | 13.03 |
| End-to-end | 78.01 | 80.21 | **81.02**(3.01↑) | 36.80 | 39.72 | **41.45**(4.65↑) | 14.35 | 5.46 | 7.53(6.82↓) |

*Fig. 8*

900

| Setting | | | | | Linear | | End-to-end | | End-to-end | |
|---|---|---|---|---|---|---|---|---|---|---|
| Method | Loss | | | | BTCV | | BTCV | | MM-WHS | |
| | $\mathcal{L}_R^l$ | $\mathcal{L}_R^g$ | $\mathcal{L}_C^{gg}$ | $\mathcal{L}_C^{gl}$ | ViT-B | ViT-T | ViT-B | ViT-T | ViT-B | ViT-T |
| Baseline | - | - | - | - | 79.04 | 77.18 | 79.61 | 78.02 | 83.85 | 83.04 |
| GL-MAE | ✓ | | | | 79.32(0.28↑) | 77.35(0.17↑) | 81.74(2.13↑) | 80.67(2.65↑) | 86.58(2.73↑) | 84.00(0.96↑) |
| | ✓ | ✓ | | | 79.79(0.75↑) | 78.20(1.02↑) | 81.77(2.16↑) | 78.70(0.68↑) | 86.77(2.92↑) | 84.14(1.10↑) |
| | ✓ | ✓ | ✓ | | 79.84(0.80↑) | 78.82(1.64↑) | 81.73(2.12↑) | 80.42(2.40↑) | 86.60(2.75↑) | 84.39(1.35↑) |
| | ✓ | ✓ | ✓ | ✓ | 79.99(0.95↑) | 78.93(1.75↑) | 81.91(2.30↑) | 80.76(2.74↑) | 87.89(4.04↑) | 84.56(1.52↑) |

*Fig. 9*

ADVANCING VOLUMETRIC MEDICAL IMAGE SEGMENTATION VIA GLOBAL-LOCAL MASKED AUTOENCODER

CROSS-REFERENCE TO RELATED APPLICATIONS

This application claims the benefit of U.S. Provisional Application No. 63/512,905, filed Jul. 10, 2023, the entirety of which is incorporated herein by reference.

BACKGROUND

Deep learning has shown great promise in medical image analysis, yet is limited to supervised learning based on a relatively large amount of labeled training data. However, labeling medical images, especially volumetric images, can be expertise-dependent, labor-intensive, and time-consuming, which motivates remarkable progress in label-efficient learning. Particularly, to enlarge the training set while keeping less human intervention, Self-Supervised Learning (SSL) approaches have demonstrated their effectiveness by firstly pretraining on a large number of unlabeled data and then finetuning on small-scale labeled datasets to improve the task performance of the small-scale labeled dataset.

SSL-based pretraining neglects the process of obtaining human annotations by learning representations with supervision signals generated from the data itself, which has become an important label-efficient solution for volumetric medical image representation learning.

Recently, Vision Transformer (ViT) has inspired an increasing number of SSL approaches due to its high scalability and generalization ability. For example, Masked Autoencoder (MAE) and SimMIM have achieved high performance in various natural image analysis tasks by learning transferable representations via reconstructing the original input in pixel from its highly-masked version based on the ViT structure. However, medical images such as Computed Tomography (CT) are often volumetric and large in size. Existing methods like Swin-UNETR and MAE3D have proposed breaking down the original volume scans into smaller sub-volumes (e.g., a 96×96×96 sub-volume from a 512×512×128 CT scan) to reduce the computation cost of ViT.

However, the use of local cropping strategies for medical images poses two significant challenges. Firstly, these strategies focus on reconstructing information from the masked local sub-volumes, neglecting the global context information of the patient as a whole. Global representation has been shown to play a crucial role in Self-Supervised Learning. For medical images, a global view of the volumetric data contains rich clinical contexts of the patient, such as the status of other organs, which is useful for further analysis and provides important clinical insights. Secondly, there is no guarantee that the learned representations will be stable to the input distortion caused by masking, particularly when the diverse local sub-volumes only represent a small portion of the original input. This can lead to slow convergence and low efficiency during training. Pretraining solely with strong augmentation, such as a local view masked with a high ratio, is considered a challenging pretext task, as it may distort the image structure and result in slow convergence. Instead, weak augmentation can be seen as a more reliable "anchor" to the strong augmentations.

SUMMARY

A first aspect of the present disclosure provides a system for training a neural network model, comprising: an image acquisition device configured to obtain volumetric image data; and a computing system in communication with the image acquisition device, wherein the computing system is configured to: obtain the volumetric image data from the image acquisition device; generate, based on the volumetric image data, images of a plurality of views, the plurality of views comprising a global complete view and one or more masked views; generate, by a Global-Local Masked Auto-Encoder (GL-MAE) encoder system, representations corresponding to the global complete view and the one or more masked views; generate, by the GL-MAE encoder system, one or more reconstructed images corresponding to the one or more masked views; evaluate, by the GL-MAE encoder system, in a shared representation space, consistency between the representations of the global complete view and the one or more masked views; compute, by the GL-MAE encoder system, one or more losses based on the one or more reconstructed images and the results from the consistency evaluation; and update, by the GL-MAE encoder system, one or more parameters in the neural network model based on the one or more losses.

According to an implementation of the first aspect, the one or more masked views comprises a global masked view and a local masked view, and the one or more reconstructed images comprises reconstructed global masked view images and reconstructed local masked view images. The one or more processors are further configured to: evaluate first consistency between the representations of the global complete view and the global masked view; and evaluate second consistency between the representations of the global complete view and the local masked view.

According to an implementation of the first aspect, the one or more processors are further configured to: project the representations of the global complete view and the one or more masked views to the shared representation space.

According to an implementation of the first aspect, the one or more losses comprises one or more reconstruction losses based on the one or more reconstructed images and one or more consistency losses based on the evaluation results.

According to an implementation of the first aspect, the one or more processors are further configured to: encode, using a first encoder, global complete view images among the received images to generate first representations corresponding to the global complete view images; and encode, using a second encoder, masked view images among the received images to generate second representations corresponding to the masked view images, wherein the first encoder is obtained based on the second encoder.

According to an implementation of the first aspect, parameters in the first encoder are updated using a momentum factor that is dynamically computed based on learnable parameters in the second encoder.

A second aspect of the present disclosure provides a method for training a neural network model, comprising: receiving, by a Global-Local Masked AutoEncoder (GL-MAE) encoder system, images of a plurality of views, the plurality of views comprising a global complete view and one or more masked views; generating, by the GL-MAE encoder system, representations corresponding to the global complete view and the one or more masked views; generating, by the GL-MAE encoder system, one or more reconstructed images corresponding to the one or more masked views; evaluating, by the GL-MAE encoder system, in a shared representation space, consistency between the representations of the global complete view and the one or more masked views; computing, by the GL-MAE encoder system, one or more losses based on the one or more reconstructed images and the results from the consistency evaluation; and updating, by the GL-MAE encoder system, one or more parameters in the neural network model based on the one or more losses.

According to an implementation of the first aspect, the one or more masked views comprises a global masked view and a local masked view, and the one or more reconstructed images comprises reconstructed global masked view images and reconstructed local masked view images.

According to an implementation of the first aspect, evaluating, in the shared representation space, consistency between the representations of the global complete view and the one or more masked views further comprises: evaluating first consistency between the representations of the global complete view and the global masked view; and evaluating second consistency between the representations of the global complete view and the local masked view.

According to an implementation of the first aspect, the method further comprises: projecting the representations of the global complete view and the one or more masked views to the shared representation space.

According to an implementation of the first aspect, the one or more losses comprises one or more reconstruction losses based on the one or more reconstructed images and one or more consistency losses based on the evaluation results.

According to an implementation of the first aspect, weight of each loss of the one or more losses is tunable.

According to an implementation of the first aspect, generating the representations corresponding to the global complete view and the one or more masked views further comprises: encoding, using a first encoder, global complete view images among the received images to generate first representations corresponding to the global complete view images; and encoding, using a second encoder, masked view images among the received images to generate second representations corresponding to the masked view images, wherein the first encoder is obtained based on the second encoder.

According to an implementation of the first aspect, parameters in the first encoder are updated using a momentum factor that is dynamically computed based on learnable parameters in the second encoder.

According to an implementation of the first aspect, the method further comprises: receiving a plurality of volumetric medical images; obtaining the images of the plurality of views by applying at least one of cropping, scaling, and downsampling; and obtaining images of the one or more masked views by applying masks with a predefined ratio.

According to an implementation of the first aspect, the method further comprises: performing, using the neural network model, segmentation on an input image to identify one or more regions of interest.

A third aspect of the present disclosure provides a non-transitory computer-readable medium, having computer-executable instructions stored thereon, for training a neural network model, the computer-executable instructions, when executed by one or more processors, causing the one or more processors to carry out: receiving images of a plurality of views, the plurality of views comprising a global complete view and one or more masked views; generating representations corresponding to the global complete view and the one or more masked views; generating one or more reconstructed images corresponding to the one or more masked views; evaluating in a shared representation space, consistency between the representations of the global complete view and the one or more masked views; computing one or more losses based on the one or more reconstructed images and the results from the consistency evaluation; and updating one or more parameters in the neural network model based on the one or more losses.

According to an implementation of the first aspect, the one or more masked views comprises a global masked view and a local masked view, and wherein the one or more reconstructed images comprises reconstructed global masked view images and reconstructed local masked view images.

According to an implementation of the first aspect, evaluating, in the shared representation space, consistency between the representations of the global complete view and the one or more masked views further comprises: evaluating first consistency between the representations of the global complete view and the global masked view; and evaluating second consistency between the representations of the global complete view and the local masked view.

According to an implementation of the first aspect, the one or more processors further carry out: projecting the representations of the global complete view and the one or more masked views to the shared representation space.

BRIEF DESCRIPTION OF THE DRAWINGS

The present systems and methods for image processing are described in detail below with reference to the attached drawing figures, wherein:

FIG. 7 presents Table 1 that shows a comparison of performances between various methods.

FIG. 8 presents Table 2 that shows a comparison of performances between various methods FIG. 9 presents Table 3 that showcases ablation study results.

DETAILED DESCRIPTION

Figure 1A:
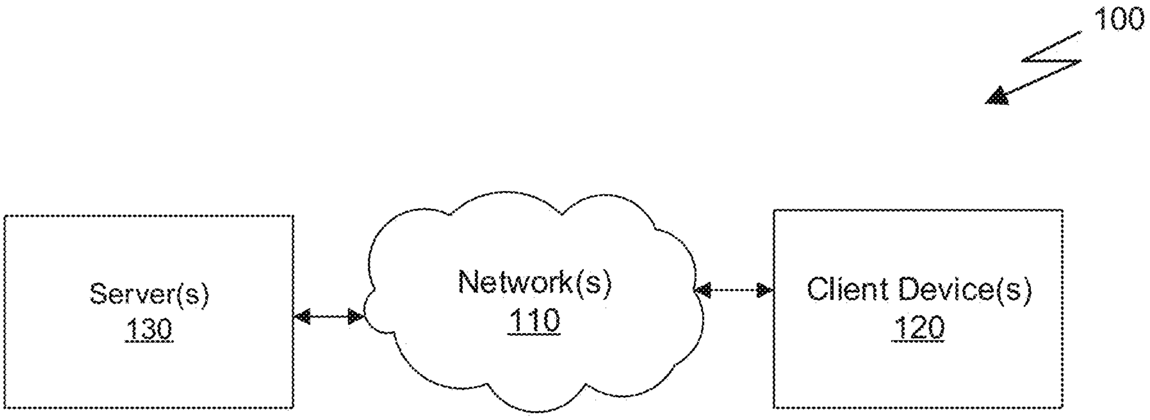
FIG. 1A illustrates an exemplary network environment, in accordance with one or more embodiments in the present disclosure.

Masked autoencoder (MAE) is a promising self-supervised pretraining technique that may improve the representation learning of a neural network without human intervention. However, applying MAE directly to volumetric medical images poses two challenges: (i) a lack of global information that is crucial for understanding the clinical context of the holistic data, (ii) no guarantee of stabilizing the representations learned from randomly masked inputs. To address these limitations, the present disclosure presents Global-Local Masked AutoEncoder (GL-MAE), an efficient and effective self-supervised pretraining strategy. In addition to reconstructing masked local views, GL-MAE incorporates global context learning by reconstructing masked global views. Furthermore, a complete global view is integrated as an anchor to guide the reconstruction and stabilize the learning process through global-to-global consistency learning and global-to-local consistency learning. Finetuning results on multiple datasets demonstrate the superiority of this method over other state-of-the-art self-supervised algorithms, highlighting its effectiveness on versatile volumetric medical image segmentation tasks, even when annotations are scarce.

In some embodiments, GL-MAE is used for learning representations of volumetric medical data. GL-MAE reconstructs input volumes from both global and local views of the data. It also employs consistency learning to enhance the semantic corresponding by using unmasked global subvolumes to guide the learning of multiple masked local and global views. By introducing the global information into the MAE-based SSL pretraining, GL-MAE achieved superior performance in the downstream volumetric medical image segmentation tasks compared with state-of-the-art techniques, such as MAE3D and Swin-UNETR.

In some embodiments, both global and local views of an input volumetric image are obtained by applying image transforms, such as cropping and downsampling. On the one hand, the global view covers a large region with rich information but low spatial resolution, which may miss details for small organs or tumors. On the other hand, the local views are rich in details but only take up a small fraction of the input volume and in high spatial resolution. To leverage both sources of information, an MAE is used to simultaneously reconstruct both the masked global and local images, enabling learning from both the global context and the local details of the data. A global view of the image encompasses a more comprehensive area of the data and could help learn representations that are invariant to different views of the same object. Such view-invariant representations are beneficial in medical image analysis. To encourage the learning of view-invariant representations, global-guided consistency learning is utilized, where the representation of an unmasked global view is used to guide learning robust representations of the masked global and local views. Finally, as the global view covers most of the local views, it serves as an "anchor" for the masked local views to learn the global-to-local consistency.

FIG. 1A illustrates an exemplary network environment 100, in accordance with one or more examples in the present disclosure. A neural network tasked for representation learning may be implemented in the exemplary network environment 100. Network environments suitable for use in implementing embodiments of the disclosure may include one or more client devices 120, servers 130, and/or other device types.

Components of a network environment may communicate with each other via a network(s) 110, which may be wired, wireless, or both. By way of example, the network 110 may include one or more Wide Area Networks (WANs), one or more Local Area Networks (LANs), one or more public networks such as the Internet, and/or one or more private networks. Where the network includes a wireless telecommunications network, components such as a base station, a communications tower, or access points (as well as other components) may provide wireless connectivity.

Compatible network environments may include one or more peer-to-peer network environments—in which case a server may not be included in a network environment—and one or more client-server network environments—in which case one or more servers may be included in a network environment. In peer-to-peer network environments, functionality described herein with respect to a server(s) may be implemented on any number of client devices.

In at least one embodiment, a network environment may include one or more cloud-based network environments, a distributed computing environment, a combination thereof, etc. A cloud-based network environment may include a framework layer, a job scheduler, a resource manager, and a distributed file system implemented on one or more of servers, which may include one or more core network servers and/or edge servers. A framework layer may include a framework to support software of a software layer and/or one or more application(s) of an application layer. The software or application(s) may respectively include web-based service software or applications. In some embodiments, one or more of the client devices may use the web-based service software or applications (e.g., by accessing the service software and/or applications via one or more application programming interfaces (APIs)). The framework layer may be, but is not limited to, a type of free and open-source software web application framework such as that may use a distributed file system for large-scale data processing (e.g., "big data").

A cloud-based network environment may provide cloud computing and/or cloud storage that carries out any combination of computing and/or data storage functions described herein (or one or more portions thereof). Any of these various functions may be distributed over multiple locations from central or core servers (e.g., of one or more data centers that may be distributed across a state, a region, a country, the globe, etc.). A cloud-based network environment may be private (e.g., limited to a single organization), may be public (e.g., available to many organizations), and/or a combination thereof (e.g., a hybrid cloud environment).

By way of example and not limitation, a client device 120 may be embodied as a Personal Computer (PC), a laptop computer, a mobile device, a smartphone, a tablet computer, or any other suitable device.

Figure 1B:
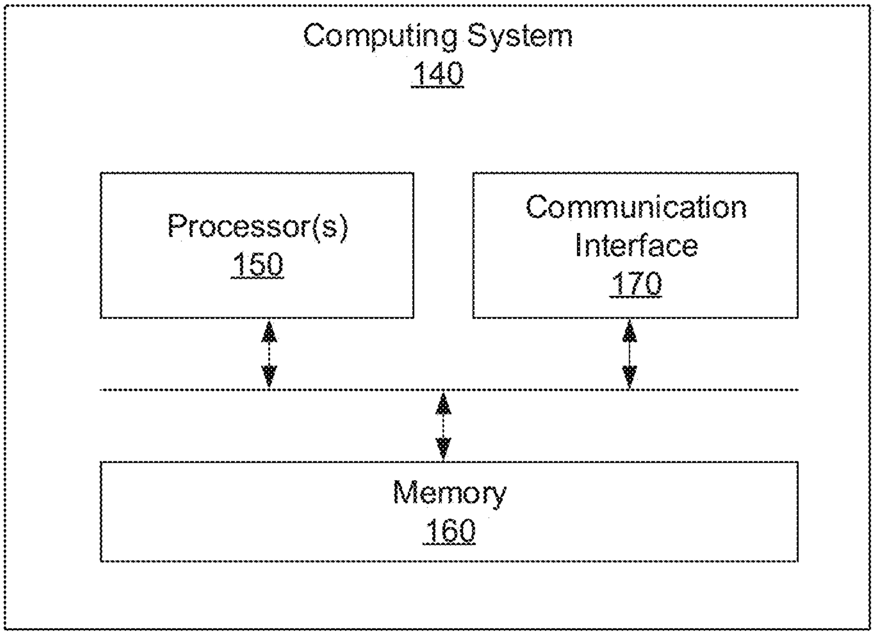
FIG. 1B is a block diagram of an exemplary computing system configured to implement various functions, in accordance with one or more embodiments in the present disclosure.

FIG. 1B is a block diagram of an exemplary computing system 140 configured to implement various functions in accordance with one or more embodiments in the present disclosure. In some examples, the computing system 140 may be embodied as a client device 120 or a server 130 as shown in FIG. 1A. In another examples, the computing system 140 may include any combination of the components in the network environment 100 as shown in FIG. 1A to carry out various functions/processes disclosed herein. In yet another examples, the computing system 140 may include a cloud storage (e.g., a network attached storage (NAS) connected in the network environment 100) storing training dataset and one or more client devices 120 and or one or more servers 130 to retrieve the training dataset from the cloud storage and train a machine learning (ML) or artificial intelligence (AI) model implemented thereon.

As shown in FIG. 1B, the computing system 140 may include one or more processors 150, a communication interface 170, and a memory 160. The one or more processors 150, communication interface 170, and memory 160 may be communicatively coupled to a bus 180 to enable communication therebetween. The processor(s) 150 may be configured to perform the operations in accordance with the instructions stored in memory 160. The processor(s) 150 may include any appropriate type of general-purpose or special-purpose microprocessor, such as central processing unit (CPU), graphic processing unit (GPU), parallel processing unit (PPU), etc. The memory 160 may be configured to store computer-readable instructions that, when executed by the processor(s) 150, can cause the processor(s) 150 to perform various operations disclosed herein. The memory 160 may be any non-transitory type of mass storage, such as volatile or non-volatile, magnetic, semiconductor-based, tape-based, optical, removable, non-removable, or other type of storage device or tangible computer-readable medium including, but not limited to, a read-only memory ("ROM"), a flash memory, a dynamic random-access memory ("RAM"), and/or a static RAM.

The communication interface 170 may be configured to communicate information between the computing system 140 and other devices or systems, such as the client device(s) 120, the server(s) 130, or any other suitable device(s)/system(s) in the network environment 100 as show in FIG. 1A. For example, the communication interface 170 may include an integrated services digital network ("ISDN") card, a cable modem, a satellite modem, or a modem to provide a data communication connection. As another example, the communication interface 170 may include a local area network ("LAN") card to provide a data communication connection to a compatible LAN. As a further example, the communication interface 170 may include a high-speed network adapter such as a fiber optic network adaptor, 10G Ethernet adaptor, or the like. Wireless links can also be implemented by the communication interface 170. In such an implementation, the communication interface 170 can send and receive electrical, electromagnetic or optical signals that carry digital data streams representing various types of information via a network. The network can typically include a cellular communication network, a Wireless Local Area Network ("WLAN"), a Wide Area Network ("WAN"), or the like. In some variations, the communication interface 170 may include various I/O devices such as a keyboard, a mouse, a touchpad, a touch screen, a microphone, a camera, a biosensor, etc. A user may input data to the computing system 140 (e.g., a terminal device) through the communication interface 170.

In some examples, a display may be integrated as part of the computing system 140 or may be provided as a separate device communicatively coupled to the computing system 140. The display may include a display device such as a Liquid Crystal Display ("LCD"), a Light Emitting Diode Display ("LED"), a plasma display, or any other type of display, and provide a Graphical User Interface ("GUI") presented on the display for user input and data depiction. In some instances, the display may be integrated as part of the communication interface 170.

In some embodiments, a ML/AL model according to exemplary embodiments of the present disclosure may be extended to any suitable type of neural network (NN) models. A NN model includes multiple layers of interconnected nodes (e.g., perceptrons, neurons, etc.) that can be trained with enormous amounts of input data to quickly solve complex problems with high accuracy. The first layer in the NN model, which receives input to the NN model, is referred to as an input layer. The last layer in the NN model, which produces outputs of the NN model, is referred to as an output layer. Any layer between the input layer and the output layer of the NN model is referred to as a hidden layer. The parameters/weights related to the NN model may be stored in a memory (e.g., a memory 160 in a computing system 140) in the form of a data structure.

Figure 2:
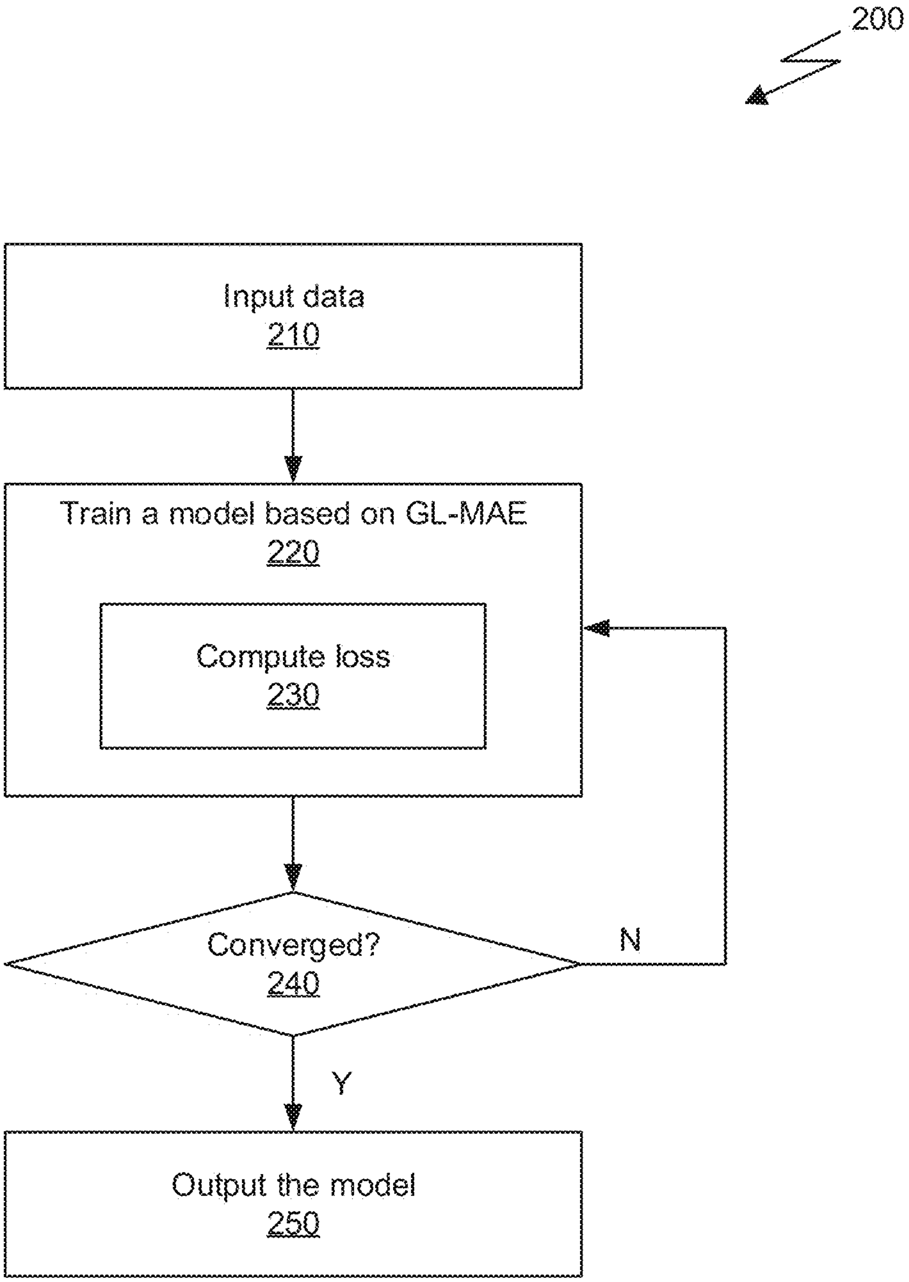
FIG. 2 is a flowchart illustrating an example process for training a neural network (NN) model, in accordance with one or more embodiments of the present disclosure.

FIG. 2 is a flowchart illustrating an example process 200 for training a NN model, in accordance with one or more embodiments of the present disclosure. The NN model may be implemented in a computing system 140 as shown in FIG. 1B operating in the network environment 100 as depicted in FIG. 1A. The computing system 140 may include one or more client devices 120, one or more servers 130, or any combination thereof in the network environment 100 as shown in FIG. 1A. One or more processer(s) 150 in the computing system 140 may execute instructions stored in the memory 160 to perform the process 200. The process 200 may be performed alone or in combination with other processes described in the present disclosure. It will be appreciated by one skilled in the art that the process 200 may be performed in any suitable environment and blocks in the process 200 may be performed in any suitable order.

At block 210, the computing system 140 obtains a dataset as input data. The dataset may be of various types, such as image data. For example, it may include volumetric medical images obtained from Computed Tomography (CT) scans, training data from data pools, augmented data from various sources, and more.

At block 220, the computing system 140 trains a NN model using the input dataset. Various techniques may be employed to train the NN model. As an illustrative example, without limiting the scope of the present disclosure, the computing system 140 may perform one or more of the following operations to train the NN model.

First, the computing system 140 initializes the NN model with random and/or default weights and biases. The weights and/or biases are parameters that may be adjusted during training. Second, the computing system 140 passes the input dataset through the model to obtain predictions. This step may be referred to as a forward pass, which involves applying the current model parameters (e.g., weights and/or biases) to the input dataset. Third, as depicted in block 230, the computing system 140 computes one or more losses. For example, the processing system applies one or more loss functions to quantify the difference between predicted and actual/target values, for example, by comparing the model's predictions to the actual/target values in the dataset. The computing system 140 backpropagates the computed loss(es) to update one or more parameters in the model. For example, the computing system 140 calculates the gradients of the loss with respect to the model parameters, thereby determining the contribution of each or some of the parameters to the error. With that, the computing system 140 adjusts one or more parameters in the model based on the computed gradients. In some instances, the computing system 140 applies suitable optimization algorithms (e.g., gradient descent) to adjust the one or more parameters in the model, aiming to minimize the loss and improve the model's performance. It will be appreciated by one skilled in the art that other techniques may be employ to utilize the computed losses for updating one or more parameters in the model. The computing system 140 performs multiple iterations or epochs to train the model. Each iteration may process a new or existing batch of data (e.g., an input dataset) and updates the model parameters, gradually improving its ability to make accurate predictions.

At block 240, the computing system 140 determines whether the trained model is converged. If not, the processing system may continue to another iteration (e.g., to perform any of blocks 210, 220, 230, and/or 240). For example, the computing system 140 may stop training when the model reaches satisfactory performance or after a predefined number of iterations or epochs.

In some examples, convergence may be determined by observing when the loss(es) of the model, measured by the loss function(s), stops decreasing significantly or starts increasing. For example, if the loss reaches a plateau or begins to rise, it suggests that the model may have converged or is overfitting. Convergence criteria may involve setting a threshold for the loss value or employing a patience parameter, which may indicate the number of iterations/epochs with no improvement before stopping the training.

At block 250, the computing system 140 outputs a model, based on determining the convergence of the model.

Figure 3:
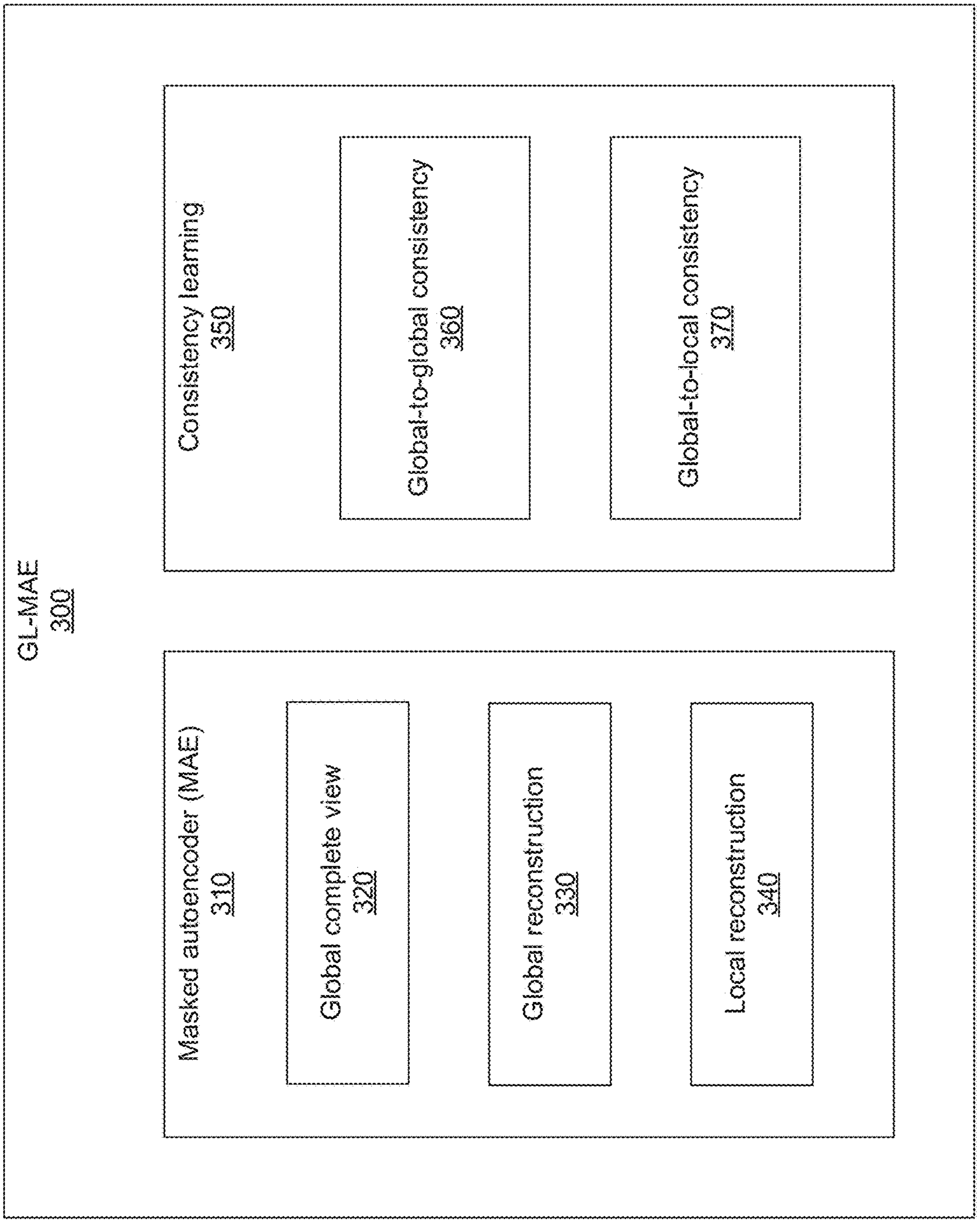
FIG. 3 is a block diagram of an exemplary Global-Local Masked AutoEncoder (GL-MAE) scheme, in accordance with one or more embodiments of the present disclosure.

FIG. 3 is a block diagram of an exemplary GL-MAE scheme 300, in accordance with one or more embodiments of the present disclosure. GL-MAE 300 may be implemented in a computing system 140 as shown in FIG. 1B operating in the network environment 100. The computing system 140 may include one or more client devices 120, one or more servers 130, or any combination thereof in the network environment 100 as shown in FIG. 1A. One or more processer(s) 150 in the computing system 140 may execute instructions stored in the memory 160 to execute any of the blocks in GL-MAE 300. GL-MAE 300 may be executed alone or in combination with other processes described in the present disclosure. It will be appreciated by one skilled in the art that GL-MAE 300 may be executed in any suitable environment and blocks in GL-MAE 300 may be executed in any suitable order.

As shown in FIG. 3, GL-MAE 300 includes various functional modules, including a masked autoencoder 310 and a consistency learning module 350. The masked autoencoder (MAE) 310 is configured to generate representations for various views (e.g., global complete views 320, masked global views, and masked local views) and perform global reconstruction 330 and local reconstruction 340 to obtain reconstructed global views and local views, respectively, based on the input image data. This enables the GL-MAE model 300 to learn global context as well as local details. The MAE 310 may include one or more encoders and/or one or more decoders. For example, one encoder may be used to encode the masked global and local views, another encoder may be used to encode the global complete views 320. The one or more encoders in the MAE 310 may be substantially the same or related. For example, the encoder used for encoding the global complete views 320 may be derived from the encoder used for encoding the masked global and local views. Similarly, one or more decoders may be employed for reconstructing the global and local views from the masked global and local views, where the one or more decoders may be the substantially the same or related.

The consistency learning module 350 is configured to learn global-to-global consistency 360 and global-to-local consistency 370 based on global guidance. In an embodiment, the global-guided consistency learning is introduced between the representations of unmasked global views (e.g., the global complete views 320) and the reconstructed masked views, which encourages invariant and robust feature learning.

In this configuration, in addition to reconstructing masked local views, GL-MAE 300 reconstructs masked local views, as well as incorporates global context learning by reconstructing masked global views. Additionally, GL-MAE 300 integrates the complete global view 320 as an anchor to guide the reconstruction and stabilize the learning process through global-to-global consistency learning 360 and global-to-local consistency learning 370. Finetuning results on multiple datasets demonstrate the superiority of this method over other state-of-the-art self-supervised algorithms, highlighting its effectiveness on versatile volumetric medical image segmentation tasks, even when annotations are scarce.

Figure 4:
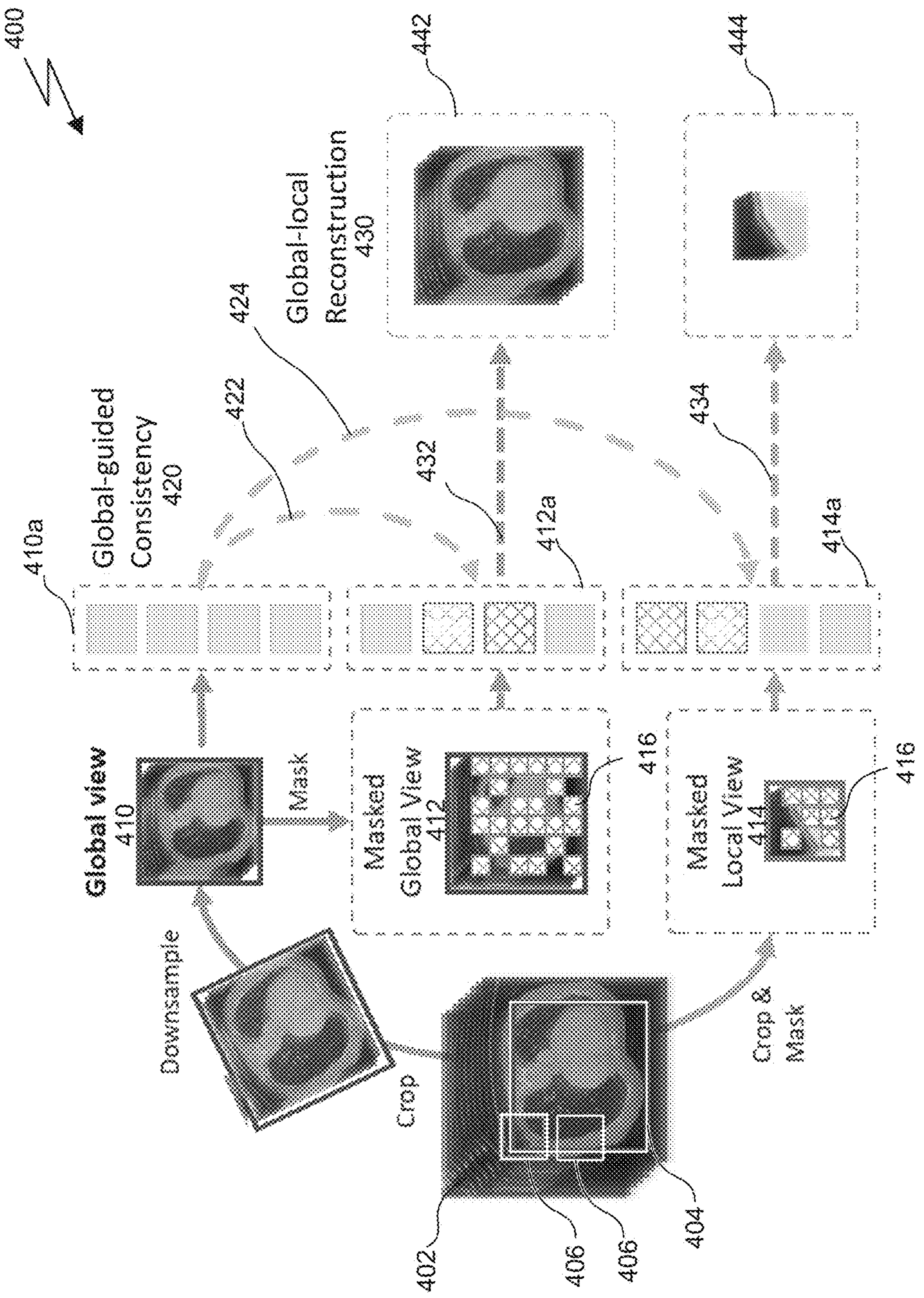
FIG. 4 illustrates an exemplary flow diagram implementing GL-MAE, in accordance with one or more embodiments of the present disclosure.

FIG. 4 illustrates an exemplary flow diagram 400 implementing GL-MAE, in accordance with one or more embodiments of the present disclosure. The flow diagram 400 may be executed on a computing system 140 as shown in FIG. 1B operating in the network environment 100. The computing system 140 may include one or more client devices 120, one or more servers 130, or any combination thereof in the network environment 100 as shown in FIG. 1A. One or more processer(s) 150 in the computing system 140 may execute instructions stored in the memory 160 to perform any of the processes as demonstrated in the flow diagram 400. The flow diagram 400 may be executed alone or in combination with other processes described in the present disclosure. It will be appreciated by one skilled in the art that the flow diagram 400 may be executed in any suitable environment and processes in the flow diagram 400 may be performed in any suitable order.

As depicted in FIG. 4, the flow diagram 400 illustrates exemplary inputs to and outputs from GL-MAE, as well as exemplary processes undergone by GL-MAE.

In this example, the inputs to GL-MAE are various views obtained from volumetric medical images 402. The various views include global view 410, masked global view 412, and masked local view 414. In some embodiment, the input image data (e.g., the volumetric medical images 402) may be transformed, such as through cropping, scaling, rotating, etc, and/or augmented. For example, the global view 410 and masked global view 412 may be obtained based on cropped image 404, while the masked local view 414 may be obtained based on cropped images 406. In one embodiment, a sub-volume of the volumetric medical images 402 may be obtained through downsampling.

Masked views, such as the masked global view 412 and masked local view 414, are generated by applying random or predefined masks (e.g., 416) to individual images. In some embodiments, Each input image, such as a global view image or a local view image, may first be segmented into multiple patches of a predefined size, for example with a predefined number of pixels. Subsequently, one or more patches in the respective image may be subjected to the application of mask(s). Masks may take various forms depending on the applications. For example, A mask may be defined as a predetermined number of pixels with default or fixed values, thereby overriding the visual information from the original image.

GL-MAE encodes the global view 410, masked global view 412, and masked local view 414 to generate corresponding representations (e.g., 410*a*, 412*a*, and 414*a*, respectively). Some or all of the patches from the input views may be encoded by GL-MAE. In some embodiments, only the patches that have not been applied with masks are encoded. The representations 410*a*, 412*a*, and 414*a* may be projected to a shared space (e.g., a shared representation space), enabling GL-MAE to learn the consistency between the representations.

Based on the representations 410*a*, 412*a*, and 414*a*, GL-MAE evaluates global-guided consistency 420 (indicated by dashed arrows 422 and 424) and performs image reconstructions 430 (indicated by dashed arrows 432 and 434). For example, the consistency learning module 350 in the GL-MAE 300 as shown in FIG. 3 performs global-to-global consistency learning 360 based on the representations 410*a* and 412*a* corresponding to the global view 410 and masked global view 412, respectively. Additionally and/or alternatively, the consistency learning module 350 in the GL-MAE 300 as shown in FIG. 3 performs global-to-local consistency learning 370 based on the representations 410*a* and 414*a* corresponding to the global view 410 and masked local view 414, respectively. Additionally, the masked auto-encoder 310 in the GL-MAE 300 as shown in FIG. 3 performs global reconstruction 330 and local reconstruction 340 based on the representations 412*a* and 414*a* corresponding to the masked global view 412 and masked local view 414, respectively.

The outputs from the GL-MAE include results from global-guided consistency learning 420 and reconstructed images (e.g., reconstructed global images 442 and/or reconstructed local images 444) from the image reconstructions 430. In some embodiments, the results from the global-guided consistency learning 420 may include one or more losses computed based on the global-to-global consistency learning 360 and/or the global-to-local consistency learning 370.

Figure 5:
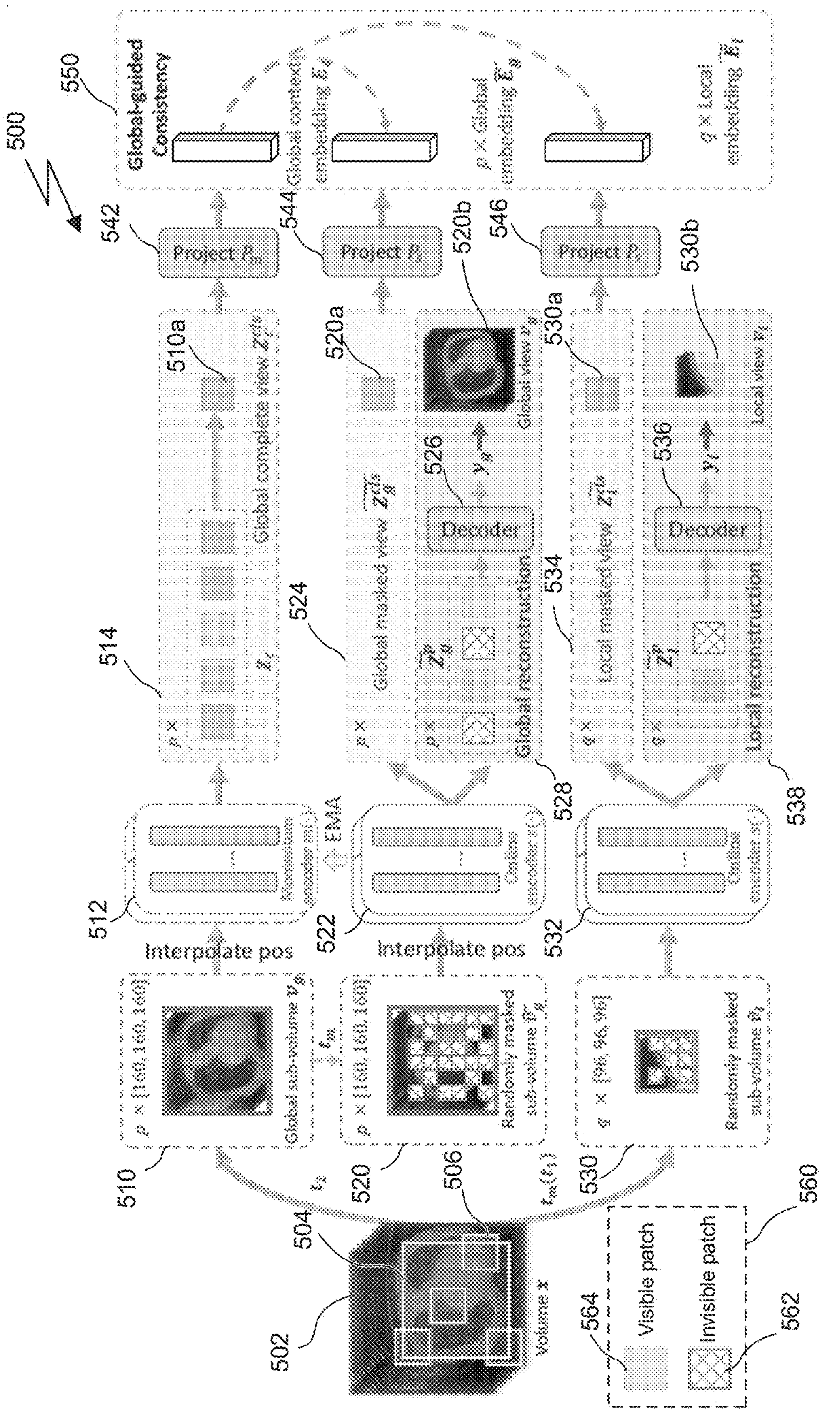
FIG. 5 illustrates an exemplary framework 500 of GL-MAE, in accordance with one or more embodiments of the present disclosure.

FIG. 5 illustrates an exemplary framework 500 of GL-MAE, in accordance with one or more embodiments of the present disclosure. The framework 500 may be implemented in a computing system 140 as shown in FIG. 1B operating in the network environment 100. The computing system 140 may include one or more client devices 120, one or more servers 130, or any combination thereof in the network environment 100 as shown in FIG. 1A. One or more processer(s) 150 in the computing system 140 may execute instructions stored in the memory 160 to perform any of the processes as demonstrated in the framework 500. The one or more processer(s) 150 in the computing system 140 may perform the processes outlined in the framework 500 to facilitate the flow diagram 400 as depicted in FIG. 4. The framework 500 may be implemented alone or in combination with other processes described in the present disclosure. It will be appreciated by one skilled in the art that the framework 500 may be implemented in any suitable environment and processes in the framework 500 may be performed in any suitable order.

As an overview of the framework 500, the initial step involves generating various views based on the input image data (e.g., volumetric medical images 502). One or more image transformations are performed on the images 502, such as cropping and downsampling. For example, cropped images 504 are used for generating global complete views (or global views in dashed box 510) and global masked views (in dashed box 520), and cropped images 506 are used for generating local masked views (in dashed box 530).

The next step is to process the various views through separate paths by using GL-MAE. The various views are processed through different paths, which may be performed in any suitable order, for example, in parallel, in series, or a combination thereof.

The global views 510 are processed by an encoder 512 to generate corresponding representations 510*a* (e.g., in dashed box 514). The global masked views 520 are processed by an encoder 522 to generate corresponding representations 520*a* (e.g., in dashed box 524). Additionally, a decoder 526 is utilized to generate reconstructed global views 520*b* (e.g., in dashed box 528). The local masked views 530 are processed by an encoder 532 to generate corresponding representations 530*a* (e.g., in dashed box 534). Additionally, a decoder 536 is utilized to generate reconstructed global views 530*b* (e.g., in dashed box 538). The encoders 522 and 532 may be substantially the same, and the decoders 526 and 536 may be substantially the same.

GL-MAE projects the representations 510*a*, 520*a*, and 530*a* to a shared space to evaluate global-guided consistency (in dashed box 550) between the representations 510*a*, 520*a*, and 530*a*.

The aforementioned processes will be further elaborated upon with exemplary equations and implementations hereinafter. It will be appreciated by one skilled in the art that these equations and implementations are merely examples and do not limit the scope of the present disclosure.

MAE with Global and Local Reconstruction

In this example, the volumetric medical images 502 include a volume (x) of images obtained from an unlabeled CT dataset (D). The unlabeled CT dataset may include raw images from CT scanning, augmented images, and/or other types of image data. The dataset (D) is represented by $D=\{x_1, \ldots, X_N\}$, where N is the total number of volumes. The N number of volumes may be used as batches of datasets for training a NN model implementing GL-MAE. As shown in FIG. 5, a volume $x \in R^{CHWD}$ is randomly sampled from D, where "CHWD" stands for the dimensions Channel, Height, Width, and Depth. The volume x is augmented into a small-scale sub-volume $v_l \in R^{CHWD}$ using image transformation $t_1$ and a large-scale sub-volume $v_g \in R^{CHWD}$ using image transformation $t_2$. The sub-volume vi comprises local view images that provide detailed information in high resolution about texture and boundaries, but lack a global view of the input data, such as the status of other organs. The sub-volume $v_l$ corresponds to a local view's set $$V_l = \{v_l^i, i \in [1, q]\}.$$

On the other hand, the sub-volume $v_g$ comprises global view images that provide a global view's set $$V_g = \{v_g^i, i \in [1, p]\}.$$

p and q are integers, which represent the number of views in the respective view's set.

In an example, for global views (e.g., in 510 and 520), images were scaled by a random ratio from the range of [0.5, 1], cropped, and then resized into [160, 160, 160] pixels in height, width, and depth dimensions. For local views (e.g., in 530), images were scaled by a random ratio from the range of [0.25, 0.5], cropped and resized into [96, 96, 96]. Finally, all images were normalized from [−1000, 1000] to [0,1]. p and q were set to 2 and 8.

To obtain the masked volumes (e.g., in 520 and 530) for local and global reconstruction, all local views 530 in the set $V_l$ and global views in the set $V_g$ 510 are individually tokenized into patches and then applied volume masking transform $t_m$ with a predefined ratio. The masked patches serve as invisible patches (562 in the legend 560), while the rest of the patches serve as visible patches (564 in the legend 560) for a learnable encoder s(•). By applying $t_m$ for each $$v_g^i \text{ and } v_l^i$$

respectively, the visible patches form a set of masked local and global sub-volumes, represented $$\tilde{V}_l = \{\tilde{v}_l^i\}, i \in [1, q] \text{ and } \tilde{V}_g = \{\tilde{v}_g^i\}, i \in [1, p],$$

respectively.

The encoder s(•) (e.g., the encoder 522/532) is used to map the input volumes (in 520/530) to a representation space. Position embedding is added to each visible patch and then combined with a class token for generating the volume representation (e.g., 520*a* or 530*a*). These visible patches for local and global views $$v_l^i \text{ and } v_g^i$$

are fed into s(•) to generate $\tilde{Z}_l$ and $\tilde{Z}_g$ by:

$$\tilde{Z}_l = s(\tilde{v}_l), \quad \text{(Eq. 1a)}$$

$$\tilde{Z}_g = s(\tilde{v}_g), \quad \text{(Eq. 1b)}$$

where Z consists of two-part embeddings, including the output of the class token and patch tokens, denoted as:

$$\tilde{Z}_l \triangleq [\tilde{Z}_l^{cls}; \tilde{Z}_l^{p}], \quad \text{(Eq. 1c)}$$

$$\tilde{Z}_g \triangleq [\tilde{Z}_g^{cls}; \tilde{Z}_g^{p}], \quad \text{(Eq. 1d)}$$

where $$\tilde{Z}_g^{cls} \text{ and } \tilde{Z}_l^{cls}$$

are outputs of the class tokens, while $$\tilde{Z}_g^{p} \text{ and } \tilde{Z}_l^{p}$$

are outputs of the visible macro-level view of a large area within the volume. In this example, position embedding are interpolated before being added to the visible tokens.

$$\tilde{Z}_g^{p} \text{ and } \tilde{Z}_l^{p}$$

are in low resolution, which is beneficial for downstream tasks involving dense prediction. This process is repeated q times for local sub-volumes and p times for global sub-volumes to patches, which then are used for reconstruction.

A momentum encoder m(•) (e.g., the encoder 512) generates a mean representation $Z_c$ (510*a* in dashed box 514) of the unmasked global view $v_g$ as:

$$Z_c = m(v_g), v_g \in V_g. \quad \text{(Eq. 1e)}$$

The momentum encoder's 512 parameters are updated using a momentum factor that is dynamically computed based on the learnable encoder's 522/532 parameters as follows:

$$m^{(t)}(\cdot) \leftarrow \mu s^{(t)}(\cdot) + (1-\mu) m^{(t-1)}(\cdot), \quad \text{(Eq. 1f)}$$

where $m^{(t)}$(•) and $s^{(t)}$(•) represents the momentum encoder and encoder at the $t^{th}$ iteration, respectively, and μ is a momentum coefficient updated with a cosine scheduler.

A decoder $\mathcal{D}$(•) (e.g., the decoder 526/536) is used to reconstruct the invisible patches from the representation of the visible patches. The input of the decoder $\mathcal{D}$(•) includes encoded visible patches and masked token. As shown in FIG. 5, the masked token is learnable and indicates the missing patches to predict. Position embedding to all tokens is added to cover the location information. The output ($y_l$, $y_g$) of the decoder D(•) is derived by:

$$y_l = \mathcal{D}(\tilde{Z}_l^{p}), \quad \text{(Eq. 2a)}$$

$$y_g = \mathcal{D}(\tilde{Z}_g^{p}). \quad \text{(Eq. 2b)}$$

Decoder output ($y_l$, $y_g$) is reshaped to form reconstructed volumes (e.g., 520*b* in dashed box 524 and 530*b* in dashed box 534). Reconstruction loss is computed using one or more loss functions. Any suitable loss functions may be used for computing the loss. For example, Mean Square Error may be used as reconstruction loss function and applied to the local and global masked sub-volumes.

Local Reconstruction

For local masked sub-volumes $\tilde{V}_l$, the local reconstruction loss $$\mathcal{L}_R^l$$

defined as:

$$\mathcal{L}_R^l = \frac{1}{|\tilde{V}_l| \times HWD} \sum_{h=1}^{H} \sum_{w=1}^{W} \sum_{d=1}^{D} \left( \sum_{v_l \in \tilde{V}_l} \frac{(y_l^{h,w,d} - v_l^{h,w,d})^2}{P} \right), \quad \text{(Eq. 3)}$$

where h, w, d denote voxel indices in the representations, P represents the number of patches for local views, and H, W, D refer to the height, width, and depth of each sub-volume, respectively. The reconstruction loss is computed as the sum of squared differences between the reconstruction target $$(v_l^{h,w,d})$$

and the reconstructed representations $$(y_l^{h,w,d})$$

by pixel values.

Global Reconstruction

For global masked sub-volumes $\tilde{V}_g$, the global reconstruction loss $$\mathcal{L}_R^g$$

is defined as:

$$\mathcal{L}_R^g = \frac{1}{|\tilde{V}_g| \times HWD} \sum_{h=1}^{H} \sum_{w=1}^{W} \sum_{d=1}^{D} \left( \sum_{v_g \in \tilde{V}_g} \frac{\left(y_g^{h,w,d} - v_g^{h,w,d}\right)^2}{P} \right), \quad \text{(Eq. 4)}$$

where P represents the number of patches for global views. Since the global view has a larger input size than local views, position embedding may be interpolated before being added to the visible tokens. This process enables the reconstruction of the masked volumes at both the local and global views, facilitating the learning of rich information from both the local details and global information.

Global-Guided Consistency

Global-guided consistency learning (e.g., block 350 in FIG. 3) includes two components: global-to-global consistency (e.g., block 360 in FIG. 3) and global-to-local consistency (e.g., block 370 in FIG. 3). The global-to-global consistency enforces consistency between the representations of the unmasked global view $v_g$ (in 510) and the masked global views $\tilde{v}_g$ (in 520), promoting the learning of features that are robust to the distortion caused by masking and accelerating training convergence. Since the global view contains richer contexts and covers most of the local views, it may be used as an "anchor" to guide the representation learning of the local views. The global-to-local consistency is used for capturing information about the relationships between different parts of an image and its main semantics. It enforces consistency between representations of learning features from the masked local views (in 530) and the mean representation of the unmasked global view (in 510). As discussed earlier, the momentum encoder's 512 parameters are updated using a momentum factor that is dynamically computed based on the learnable encoder's 522/532 parameters.

To perform consistency learning, the representations of $$Z_l^{cls},$$

the masked global views $$\tilde{Z}_g^{cls},$$

and the masked local views $$\tilde{Z}_l^{cls}$$

are first projected into a shared space. In some embodiments, the projection is performed by projection layers $P_s(\bullet)$ (denoted as 544/546 in FIG. 5) and $P_m(\bullet)$ (denoted as 542 in FIG. 5), which are connected to the output of the encoders s(•) 522/532 and m(•) 512, respectively. In further embodiments, the projections are implemented using multiple fully-connected layers followed by an activation function. For example, a Gaussian Error Linear Unit activation function may be used. After projection, the embeddings of the complete global views, the masked global views, and the masked local view are obtained as:

$$E_c = \mathcal{P}_m\left(Z_c^{cls}\right), \quad \text{(Eq. 5a)}$$

$$\tilde{E}_g = \mathcal{P}_s\left(\tilde{Z}_g^{cls}\right), \quad \text{(Eq. 5b)}$$

$$\tilde{E}_l = \mathcal{P}_s\left(\tilde{Z}_l^{cls}\right), \quad \text{(Eq. 5c)}$$

where $E_c$ represents the embedding of the complete global views, $\tilde{E}_g$ represents the embedding of the masked global views, and Et represents the embedding of the masked local view. The dimension of $E_c$, $E_g$ and $\tilde{E}_l$ is represented by K, which is a predefined value, e.g., 512. For each type of embedding E in the shared space, it is normalized before computing the loss function. The embedding $E^i$ is normalized as follows:

$$\Gamma\left(E^i\right) = \frac{\exp\left(E^i/t\right)}{\sum_{k=1}^{K} \exp\left(E^k/t\right)}, \quad \text{(Eq. 6)}$$

where t represents the temperature used to control the entropy of the distribution. The training of GL-MAE may aim to minimize the distributions between the embedding representations of the global complete view $E_c$ and the masked global view $\tilde{E}_g$, and the distributions between the embedding representations of the global complete view $E_c$ and the masked local view $\tilde{E}_l$ by minimizing:

$$H\left(\Gamma(E_c), \Gamma(\tilde{E}_g)\right) + H\left(\Gamma(E_c), \Gamma(\tilde{E}_l)\right), \quad \text{(Eq. 7)}$$

where H(x, y)=−x log y is cross-entropy loss.

Global-to-Global Consistency

For global unmasked sub-volumes $V_g$ and global masked sub-volumes $\tilde{V}_g$, a global-to-global consistency loss function is formulated as:

$$\mathcal{L}_C^{gg} = \frac{1}{|V_g| \cdot |\tilde{V}_g|} \left\{ \sum_{v_g \in V_g} \sum_{\tilde{v}_g \in \tilde{V}_g} H\left(\Gamma(E_c), \Gamma(\tilde{E}_g)\right) \right\}, \quad \text{(Eq. 8)}$$

where the operator |•| computes the number of volumes in the respective set. $\tilde{E}_g$ learns consistency guided by the global context embedding $E_c$.

Global-to-Local Consistency

For global unmasked sub-volumes $V_g$ and local masked volumes $V_l$, a global-to-local consistency loss function is formulated as:

$$\mathcal{L}_C^{gl} = \frac{1}{|V_g| \cdot |\tilde{V}_l|} \left\{ \sum_{v_g \in V_g} \sum_{\tilde{v}_l \in \tilde{V}_l} H\left(\Gamma(E_c), \Gamma(\tilde{E}_l)\right) \right\}. \quad \text{(Eq. 9)}$$

Local embedding $\tilde{E}_l$ learn consistency guided by global context embedding $E_c$ during the pretraining process.

Overall Loss Function

The overall loss function is represented by:

$$\mathcal{L} = \mathcal{L}_R^l + \beta_1 \mathcal{L}_R^g + \beta_2 \mathcal{L}_C^{gg} + \beta_3 \mathcal{L}_C^{gl}, \quad \text{(Eq. 10)}$$

where $\beta_1$, $\beta_2$, and $\beta_3$ are hyper-parameters, which are used to balance the relative contributions of these four loss terms.

The values of $\beta_1$, $\beta_2$, and/or $\beta_3$ may be tuned according to various usage scenarios. In some embodiments, $\beta_1$, $\beta_2$, and $\beta_3$ are set to 1.0 in experiments empirically.

Figure 6:
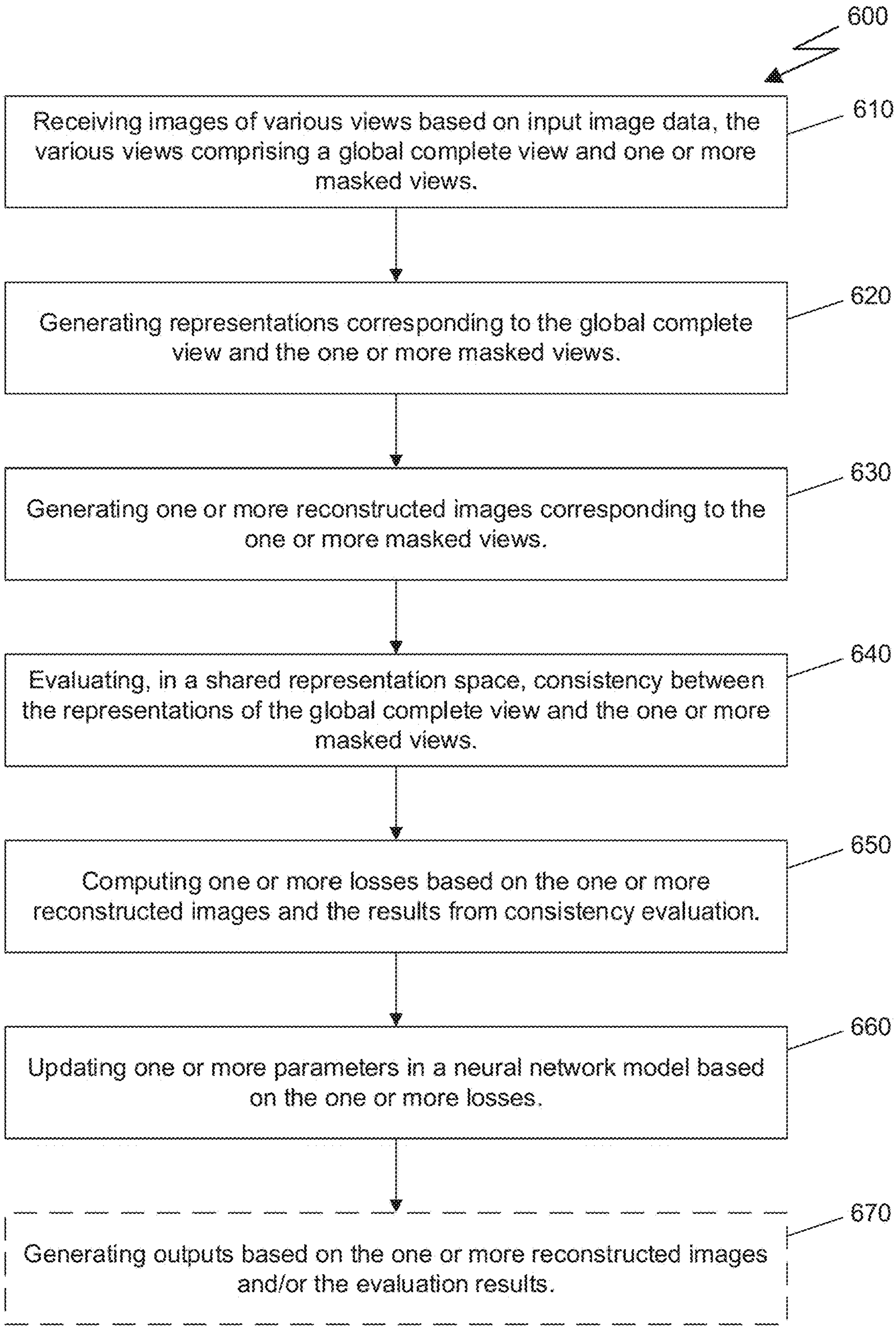
FIG. 6 is a block diagram of an exemplary process implementing GL-MAE, in accordance with one or more embodiments of the present disclosure.

FIG. 6 is a block diagram of an exemplary process 600 implementing GL-MAE, in accordance with one or more embodiments of the present disclosure. The process 600 may be performed by a computing system 140 as shown in FIG. 1B operating in the network environment 100. GL-MAE is implemented on the computing system 140. The computing system 140 may include one or more client devices 120, one or more servers 130, or any combination thereof in the network environment 100 as shown in FIG. 1A. One or more processer(s) 150 in the computing system 140 may execute instructions stored in the memory 160 to perform any of the blocks as demonstrated in the process 600. The one or more processer(s) 150 in the computing system 140 may perform the process 600 to facilitate the flow diagram 400 as depicted in FIG. 4 and/or the framework 500 as demonstrated in FIG. 5. The process 600 may be performed alone or in combination with other processes described in the present disclosure. It will be appreciated by one skilled in the art that the process 600 may be performed in any suitable environment and blocks in the process 600 may be performed in any suitable order.

At block 610, the computing system receives images of various views based on input image data. The various views include a global complete view, and one or more masked views. In an embodiment, the one or more masked views includes a global masked view and a local masked view.

At block 620, the computing system generates representations corresponding to the global complete view and the one or more masked views.

At block 630, the computing system generates one or more reconstructed images corresponding to the one or more masked views.

At block 640, the computing system evaluates, in a shared representation space, consistency between the representations of the global complete view and the one or more masked views. For example, the computing system projects the representations of the global complete view and the one or more masked views to the shared representation space for evaluation. In some embodiments, the computing system evaluates first consistency between the representations of the global complete view and the global masked view, and second consistency between the representations of the global complete view and the local masked view.

At block 650, the computing system computes one or more losses based on the one or more reconstructed images and the results from the consistency evaluation.

When blocks 610-650 are performed during training of a NN model implementing GL-MAE, the computing system updates one or more parameters in the NN model based on the one or more losses (e.g., as indicated in block 660).

During inference, the computing system generates outputs based on the one or more reconstructed images and/or the evaluation results, (e.g., as indicated in dashed block 670).

The trained NN model with GL-MAE may be applied to various tasks, including image segmentation and disease classification. For image segmentation, the NN model with GL-MAE effectively segments CT scans or Magnetic Resonance Imaging (MRI) scans by identifying areas of interest such as diseased organs and tumor regions. In disease classification, the NN model with GL-MAE provides accurate diagnostic results based on CT scans or MRI scans, including the diagnosis of Covid-19.

In some embodiments, the computing system is communicatively connected to one or more image acquisition devices. The image acquisition device(s) is configured to obtain volumetric image data and transmit the data to the computing system for data processing, for example, through the communication interface 170. The image acquisition devices may include various cameras, a CT scanner, or an MRI scanner.

The following provides exemplary pseudocodes for implementing one or more processes discussed above. For example, Algorithm 1 may be used for generating various views as input to GL-MAE.

Algorithm 1 Pseudocode of data augmentation in PyTorch-like style.

```
# Input: volume, global_scale_factor, local_scale_factor,
local_crop_numbers, global_size,
local_size
$ Output: crops
# volume: loading a sample from the 3D CT datasat used for pretraining,
which has been processed by spacing, scaleIntensity etc.
# global_scale_factor, local_scale_factor: factors to scale the image.
# local_crop_numbers: numbers of cropped volume, e.g., 8.
# global_size, local_size: size for global and local sub Volume.
# Define transforms for generating local and global sub volumes
local_transform = Compose([
    RandScaleCropd(local_scale_factor), Resized(local_size)])
global_transform = Compose([
    RandScaleCropd(global_scale_factor), Resized(global_size)]
crops = [ ] # Process of generating the expected sub volumes
crops.append([global_transforms(volume), global_transforms(volume)])
for iter in range(local_crop_numbers):
  crops.append(local_transform(volume))
```

Algorithm 2 may be used for implementing GL-MAE in pretraining.

Algorithm 2 Pseudocode of proposed SSL pretraining in PyTorch-like style.

```
# Input: loader/encoder/decoder/m_encoder/proj_m/proj_s and
hyper-parameters etc.
$ Output: encoder
# loader: 3D CT dataloader for pretraining
# encoder/decoder/m_encoder/proj_m/proj_s: model used for
pre-training/reconstruct/project
# m: momentum factor. mask_ratio
# Initialization, encoder with mask ratio, momentum w/o mask ratio
m_encoder.params = encoder.params
for epoch in range(n_epochs):
  for xs in loader:
    g_xs, l_xs = aug(xs) # augmented with the defined data
    augmentation transform
    # Obtain masked global and local feature from encoder with
    mask_ratio
    g_features, l_features = encoder.forward([g_xs, l_xs], mask_ratio)
    # Reconstruct global and local volume from decoder
    g_volume, l_volume = decoder.forward([g_features, l_features])
    s_g_feature, s_l_feature = proj_s.forward([g_features,
    l_features])
    m_g_features = m_encoder.forward(g_xs, mask_ratio=0) #Obtain
global volume feature
    m_g_features = proj_m.forward(m_g_features)
    # Optimized with the following losses
    $\mathcal{L}_{\mathcal{R}}$ with [g_xs, l_xs, g_volume, l_volume] computed by Equations
    3 and 4
    $\mathcal{L}_{\mathcal{C}}$ with [m_g_features, s_g_feature, s_l_feature] computed by
    Equations 8 and 9
    $\mathcal{L} = \mathcal{L}_{\mathcal{R}} + \alpha \mathcal{L}_{\mathcal{C}}$
    $\mathcal{L}$.backward( )
    update(encoder, decoder, proj_m, proj_s)
    m_encoder = (1-m) * m_encoder.params + m * encoder.params
```

Illustrative experimental results are described in detail below to demonstrate efficacy and advantages of the present disclosure. Additional details and advantages relating to exemplary embodiments of the present disclosure are discussed by Zhuang et al. in "ADVANCING VOLUMETRIC MEDICAL IMAGE SEGMENTATION VIA GLOBAL-LOCAL MASKED AUTOENCODER," (available at arXiv: 2306.08913), which is hereby incorporated by reference in its entirety.

Datasets and Evaluation Metrics

The SSL pretraining experiments were carried out on the Beyond the Cranial Vault (BTCV) abdomen challenge dataset (Landman et al. 2015) and TCIA Covid19 dataset (An et al. 2020). For downstream tasks, experiments were mainly conducted on the BTCV dataset to follow previous work (Chen et al. 2023; Tang et al. 2022). To assess the model's generalization on Computed Tomography (CT) datasets, its effectiveness was also evaluated on MM-WHS (Zhuang 2018), Medical Segmentation Decathlon (MSD) Task 09 Spleen, and The COVID-19-20 Lung CT Lesion Segmentation Challenge dataset (Covid-19-20 dataset) (Roth et al. 2022). The model was further transferred to Brain Tumor Segmentation (BrasTS) (Simpson et al. 2019) for assessing its cross-modality generalization ability. All datasets used were collected from open source and can be obtained via the cited papers. Dice Score (%) was used as the evaluation metric following (Chen et al. 2023; Tang et al. 2022).

Pretraining Setting

ViT is used as a transformer-based backbone. Both ViT-Tiny (ViT-T) and ViT-Base (ViT-B) were used for the experiments. The pretraining phase was conducted for 1600 epochs for ViT-T and ViT-B without specification, with an initial learning rate of 1e-2, employing AdamW (Kingma and Ba 2014) as an optimizer and a batch size of 256 on four 3090Ti for 3 days. For global views (e.g., $v_g$ in 510 and 520 in FIG. 5), images were scaled by a random ratio from the range of [0.5, 1], cropped, and then resized into [160, 160, 160], while for local views (e.g., $v_l$ in 530 in FIG. 5), images were scaled by a random ratio from the range of [0.25, 0.5], cropped and resized into [96, 96, 96]. Finally, all images were normalized from [−1000, 1000] to [0, 1]. p and q were set to 2 and 8, respectively.

Finetuning Setting

UNETR (Hatamizadeh et al. 2022) is adopted as the segmentation framework. Finetuning is performed on BTCV dataset. For linear evaluation that freezes the encoder parameters and finetuning the segmentation decoder head, model was finetuned for 3000 epochs using an initial learning rate of 1e-2, and trained on a single 3090Ti GPU with a batch size of 4. For end-to-end segmentation, the model was trained on four 3090Ti GPUs for 3000 epochs, with a batch size of 4, using an initial learning rate of 3e-4.

Experiment Results on Downstream Tasks

End-to-end and linear evaluation. To assess the effectiveness of this method, following (Tang et al. 2022; Chen et al. 2023; He et al. 2023), end-to-end segmentation experiments were conducted on three datasets. FIG. 7 presents Table 1 (700) that shows a comparison of performances between various methods. SL represents Supervised Learning.

As shown in Table 1 (700), GL-MAE (10th row) outperformed the Supervised baseline (3rd row) by a large margin (82.33% vs 79.61%, 95.72% vs 94.20%, and 88.88% vs 83.85%) with full training dataset, indicating that GL-MAE benefits the model from the unlabeled dataset. MAE3D is a recently proposed competitive SSL strategy in medical image analysis, where it has shown superiority (9th row), particularly on dense prediction tasks such as segmentation. GL-MAE (10th row) outperformed the MAE3D (9th row), which further confirms the its effectiveness. SegresNet and 3D U-Net are supervised models with competitive performance. Swin-UNETR uses 3D Swin-Transformer as the backbone, while GLSV was designed for Cardiac CT images. All SSL methods (4-10th rows) achieved better performance than the supervised Baseline, while GL-MAE (10th row) achieved the best performance over three datasets even when using only 25% and 50% annotations of the training datasets. This indicates the superior generalization ability of GL-MAE.

GL-MAE showed consistent performance when using a more lightweight transformer, ViT-T, which requires less computational resources and can be trained and inferred faster. FIG. 8 presents Table 2 (800) that shows a comparison of performances between various methods.

As shown in Table 2 (800), GL-MAE outperformed other methods by a large margin in terms of average Dice score, Normalized surface dice, and Hausdorff distance metric in both linear and end-to-end segmentation evaluation settings. This demonstrates the versatility of GL-MAE when adapting to a lightweight backbone, which is necessary in certain situations such as surgical robots.

Generalization on the unseen datasets. MM-WHS is a pre-dominant small-scale organ dataset that has not been involved in the pretraining. The experimental findings demonstrated that GL-MAE significantly improved the average dice score compared with the MAE3D, indicating its strong generalization capabilities. Furthermore, there were substantial enhancements in the performance of the aorta, LV, and RV, which share analogous structural features with the training data. This suggests that GL-MAE can exploit the structural consistency between organs across varying datasets and generalize effectively to the novel unseen datasets.

COVID-19 lesion segmentation. CT scans are commonly used in diagnosing COVID-19, yet there is a shortage of annotated data. GL-MAE has shown to improvement in COVID-19 lesion segmentation performance, indicating that GL-MAE can capture valuable knowledge from unlabeled CT datasets to improve disease diagnosis, demonstrating the versatility of the proposed method in practical clinical settings.

GL-MAE may be applied to other downstream tasks for other applications, such as processing Magnetic Resonance Imaging (MRI) datasets.

Analysis of the Framework

Ablation study. The framework 500 as demonstrated in FIG. 5 was studied. To better understand each loss term's (e.g., in Equation 10) impact, an ablation study of the global and local terms for both reconstructions and global-guided consistency learning was conducted. FIG. 9 presents Table 3 (900) that showcases the ablation studies conducted on the BTCV validation datasets under both linear and end-to-end segmentation settings, as well as on the MM-WHS under end-to-end segmentation.

ViT-B and ViT-T were both considered as the backbone of the framework 500. The first row represents the supervised baseline without any related strategies. Instead of reconstructing the local patches at a time in each iteration, in the 2nd row, the GL-MAE method firstly reconstructs the local patches q times each iteration, thereby learning rich representation and exhibiting better performance most of the time. In the 3rd row, the reconstruction for global patches was used, further improving performance since the model can learn the global context as well as the local details. In the 4th row, the global-to-global consistency was introduced to learn a more robust representation of distortion caused by masking and learn the critical information, leading to further performance improvement. The last row represents the global-local consistency, which aims to capture the relationship between different parts of the images and their main semantics. The final objective loss function achieved the best performance across several datasets with various settings, demonstrating the importance of global information for volumetric data.

Label-efficient finetuning. An evaluation of GL-MAE was conducted under a semi-supervised learning scheme with ViT-T as the backbone. The experimental results suggested that GL-MAE can improve the dice score even when the amount of annotated training data is limited. Transformer-based models are prone to over-fitting the limited labeled data due to their dense connections, while GL-MAE can reduce the necessity for labeled data and effectively enhance performance even in low-annotated learning scenarios.

Convergence comparison. GL-MAE exhibits faster convergence and superior performance compared to MAE3D. This suggests that pretraining with global complete views and masked views can help stabilize the training process, resulting in faster convergence and more powerful representation. By utilizing global complete views as an "anchor" for local and global masked views, the model establishes a stronger relationship through global-guided consistency. The integration of global context information and different scale reconstructions enhances the overall performance of GL-MAE and contributes to its superior results.

Analysis of mask ratio. The impact of the mask ratio for the reconstruction of GL-MAE was studied. The findings showed that the mask ratio may be adjusted to balance between preserving important information and providing enough diversity for the model to learn robust representations.

Scaling to larger data. Experimental results demonstrated the ability of GL-MAE to scale to larger amounts of data and improve performance on downstream tasks.

Visualization. Studies showed that GL-MAE can improve the completeness of segmentation results (e.g., patches in the reconstructed global and local images). For example, some experiments showed that the results of segmentation using GL-MAE were better than those using MAE3D and Swin-UNETR, particularly in terms of completeness for larger organs.

It is noted that the techniques described herein may be embodied in executable instructions stored in a non-transitory computer readable medium for use by or in connection with a processor-based instruction execution machine, system, apparatus, or device. It will be appreciated by those skilled in the art that, for some embodiments, various types of computer-readable media can be included for storing data. As used herein, a "computer-readable medium" includes one or more of any suitable media for storing the executable instructions of a computer program such that the instruction execution machine, system, apparatus, or device may read (or fetch) the instructions from the computer-readable medium and execute the instructions for carrying out the described embodiments. Suitable storage formats include one or more of an electronic, magnetic, optical, and electromagnetic format. A non-exhaustive list of conventional exemplary computer-readable medium includes: a portable computer diskette; a random-access memory (RAM); a read-only memory (ROM); an erasable programmable read only memory (EPROM); a flash memory device; and optical storage devices, including a portable compact disc (CD), a portable digital video disc (DVD), and the like.

It should be understood that the arrangement of components illustrated in the attached Figures are for illustrative purposes and that other arrangements are possible. For example, one or more of the elements described herein may be realized, in whole or in part, as an electronic hardware component. The elements may be implemented in software, hardware, or a combination of software and hardware. Moreover, some or all of these other elements may be combined, some may be omitted altogether, and additional components may be added while still achieving the functionality described herein. Thus, the subject matter described herein may be embodied in many different variations, and all such variations are contemplated to be within the scope of the claims.

To facilitate an understanding of the subject matter described herein, many aspects are described in terms of sequences of actions. It will be recognized by those skilled in the art that the various actions may be performed by specialized circuits or circuitry, by program instructions being executed by one or more processors, or by a combination of both. The description herein of any sequence of actions is not intended to imply that the specific order described for performing that sequence must be followed. All methods described herein may be performed in any suitable order unless otherwise indicated herein or otherwise clearly contradicted by context.

The use of the terms "a" and "an" and "the" and similar references in the context of describing the subject matter (particularly in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. Furthermore, the foregoing description is for the purpose of illustration only, and not for the purpose of limitation, as the scope of protection sought is defined by the claims as set forth hereinafter together with any equivalents thereof. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

The invention claimed is:

1. A system for training a neural network model, comprising:

an image acquisition device configured to obtain volumetric image data; and a computing system in communication with the image acquisition device, wherein the computing system comprises one or more processors configured to:

obtain the volumetric image data from the image acquisition device;

generate, based on the volumetric image data, images of a plurality of views, the plurality of views comprising a global complete view and one or more masked views;

generate, by a Global-Local Masked AutoEncoder (GL-MAE) encoder system, representations of the global complete view and the one or more masked views;

generate, by the GL-MAE encoder system, one or more reconstructed images corresponding to the one or more masked views;

evaluate, by the GL-MAE encoder system, in a shared representation space, consistency between the representations of the global complete view and the one or more masked views;

compute, by the GL-MAE encoder system, one or more losses based on the one or more reconstructed images and the results from the consistency evaluation; and update, by the GL-MAE encoder system, one or more parameters in the neural network model based on the one or more losses;

wherein the one or more masked views comprise a global masked view and a local masked view, wherein the one or more reconstructed images comprise reconstructed global masked view images and reconstructed local masked view images, and wherein the one or more processors are further configured to:

evaluate first consistency between the representations of the global complete view and the global masked view; and evaluate second consistency between the representations of the global complete view and the local masked view.

2. The system of claim 1, wherein the one or more processors are further configured to:

project the representations of the global complete view and the one or more masked views to the shared representation space.

3. The system of claim 1, wherein the one or more losses comprise one or more reconstruction losses based on the one or more reconstructed images and one or more consistency losses based on the evaluation results.

4. The system of claim 1, wherein the one or more processors are further configured to:

encode, using a first encoder, global complete view images to generate first representations of the global complete view images, wherein the global complete view images are images of the global complete view; and encode, using a second encoder, masked view images to generate second representations of the masked view images, wherein the masked view images are images of the one or more masked views; and wherein the first encoder is obtained based on the second encoder.

5. The system of claim 4, wherein the one or more processors are further configured to:

update, based on the one or more losses, learnable parameters in the second encoder;

compute, dynamically based on the learnable parameters in the second encoder, a momentum factor; and update, based on the momentum factor, one or more parameters in the first encoder.

6. A method for training a neural network model, comprising:

receiving, by a Global-Local Masked AutoEncoder (GL-MAE) encoder system, images of a plurality of views, the plurality of views comprising a global complete view and one or more masked views;

generating, by the GL-MAE encoder system, representations of the global complete view and the one or more masked views;

generating, by the GL-MAE encoder system, one or more reconstructed images corresponding to the one or more masked views;

evaluating, by the GL-MAE encoder system, in a shared representation space, consistency between the representations of the global complete view and the one or more masked views;

computing, by the GL-MAE encoder system, one or more losses based on the one or more reconstructed images and the results from the consistency evaluation; and updating, by the GL-MAE encoder system, one or more parameters in the neural network model based on the one or more losses;

wherein generating the representations of the global complete view and the one or more masked views further comprises:

encoding, using a first encoder, global complete view images to generate first representations of the global complete view images, wherein the global complete view images are images of the global complete view; and encoding, using a second encoder, masked view images to generate second representations of the masked view images, wherein the masked view images are images of the one or more masked views; and wherein the first encoder is obtained based on the second encoder.

7. The method of claim 6, wherein the one or more masked views comprise a global masked view and a local masked view, and wherein the one or more reconstructed images comprise reconstructed global masked view images and reconstructed local masked view images.

8. The method of claim 7, wherein evaluating, in the shared representation space, consistency between the representations of the global complete view and the one or more masked views further comprises:

evaluating first consistency between the representations of the global complete view and the global masked view; and evaluating second consistency between the representations of the global complete view and the local masked view.

9. The method of claim 6, further comprising:

projecting the representations of the global complete view and the one or more masked views to the shared representation space.

10. The method of claim 6, wherein the one or more losses comprise one or more reconstruction losses based on the one or more reconstructed images and one or more consistency losses based on the evaluation results.

11. The method of claim 10, wherein a weight of each loss of the one or more losses is tunable.

12. The method of claim 6, wherein updating, by the GL-MAE encoder system, the one or more parameters in the neural network model based on the one or more losses comprises:

updating, based on the one or more losses, learnable parameters in the second encoder:

computing, dynamically based on the learnable parameters in the second encoder, a momentum factor; and updating, based on the momentum factor, one or more parameters in the first encoder.

13. The method of claim 6, further comprising:

receiving a plurality of volumetric medical images;

obtaining the images of the plurality of views by applying at least one of cropping, scaling, and downsampling; and obtaining the images of the one or more masked views by applying masks with a predefined ratio.

14. The method of claim 6, further comprising:

performing, using the neural network model, segmentation on an input image to identify one or more regions of interest.

15. A non-transitory computer-readable medium having computer-executable instructions stored thereon for training a neural network model, the computer-executable instructions, when executed by one or more processors, causing the one or more processors to carry out:

receiving images of a plurality of views, the plurality of views comprising a global complete view and one or more masked views;

generating representations of the global complete view and the one or more masked views;

generating one or more reconstructed images corresponding to the one or more masked views;

evaluating in a shared representation space, consistency between the representations of the global complete view and the one or more masked views;

computing one or more losses based on the one or more reconstructed images and the results from the consistency evaluation; and updating one or more parameters in the neural network model based on the one or more losses;

wherein the one or more masked views comprise a global masked view and a local masked view, and wherein the one or more reconstructed images comprise reconstructed global masked view images and reconstructed local masked view images; and wherein evaluating, in the shared representation space, consistency between the representations of the global complete view and the one or more masked views further comprises:

evaluating first consistency between the representations of the global complete view and the global masked view; and evaluating second consistency between the representations of the global complete view and the local masked view.

16. The non-transitory computer-readable medium of claim 15, wherein the computer-executable instructions, when executed by the one or more processors, further cause the one or more processors to carry out:

projecting the representations of the global complete view and the one or more masked views to the shared representation space.

17. The system of claim 1, wherein the image acquisition device comprises a camera, a computed tomography (CT) scanner, or a magnetic resonance imaging (MRI) scanner.

18. The non-transitory computer-readable medium of claim 15, wherein the one or more losses comprise one or more reconstruction losses based on the one or more reconstructed images and one or more consistency losses based on the evaluation results.

19. The non-transitory computer-readable medium of claim 18, wherein a weight of each loss of the one or more losses is tunable.

20. The non-transitory computer-readable medium of claim 6, wherein generating the representations of the global complete view and the one or more masked views further comprises:

encoding, using a first encoder, global complete view images to generate first representations of the global complete view images, wherein the global complete view images are the images of the global complete view; and encoding, using a second encoder, masked view images to generate second representations of the masked view images, wherein the masked view images are the images of the one or more masked views; and wherein the first encoder is obtained based on the second encoder.

* * * * *